(12) United States Patent
Acker et al.

(10) Patent No.: US 6,605,084 B2
(45) Date of Patent: Aug. 12, 2003

(54) APPARATUS AND METHODS FOR INTRABODY THERMAL TREATMENT

(75) Inventors: David E. Acker, Setauket, NY (US); Patrick David Lopath, Setauket, NY (US); Todd Fjield, Port Jefferson Station, NY (US); Keith A. Reisinger, Miami Lakes, FL (US)

(73) Assignee: Transurgical, Inc., Setauket, NY (US)

( * ) Notice: Subject to any disclaimer, the term of this patent is extended or adjusted under 35 U.S.C. 154(b) by 304 days.

(21) Appl. No.: 09/815,863

(22) Filed: Mar. 23, 2001

(65) Prior Publication Data

US 2002/0002371 A1 Jan. 3, 2002

Related U.S. Application Data

(60) Provisional application No. 60/192,074, filed on Mar. 24, 2000.

(51) Int. Cl.$^7$ ................................................ A61B 18/04
(52) U.S. Cl. .................... 606/28; 600/459; 600/466; 607/113; 606/96
(58) Field of Search ................................ 606/7, 27, 28, 606/96; 600/437, 459, 462, 463, 466, 467, 472; 607/96, 113

(56) References Cited

U.S. PATENT DOCUMENTS

| | | | |
|---|---|---|---|
| 4,718,421 A | | 1/1988 | Rohwedder et al. |
| 5,509,417 A | * | 4/1996 | Dias et al. .................. 600/459 |
| 5,575,766 A | | 11/1996 | Swartz et al. |
| 5,582,609 A | | 12/1996 | Swanson et al. |
| 5,590,657 A | * | 1/1997 | Cain et al. .................. 600/463 |
| 5,630,837 A | | 5/1997 | Crowley |
| 5,704,361 A | | 1/1998 | Seward et al. |
| 5,938,660 A | | 8/1999 | Swartz et al. |
| 5,971,983 A | | 10/1999 | Lesh |
| 6,024,703 A | * | 2/2000 | Zanelli et al. .............. 600/459 |
| 6,149,599 A | * | 11/2000 | Schlesinger et al. ......... 600/437 |
| 6,451,044 B1 | * | 9/2002 | Naghavi et al. .............. 607/96 |
| 6,475,210 B1 | * | 11/2002 | Phelps et al. .................. 606/7 |

FOREIGN PATENT DOCUMENTS

| | | |
|---|---|---|
| EP | 1 042 990 A | 10/2000 |
| GB | 2 321 853 A | 12/1998 |
| WO | WO 95/01751 A | 1/1995 |
| WO | WO 99/33391 A | 7/1998 |
| WO | 98/52465 WO | 11/1998 |
| WO | 99/02096 WO | 1/1999 |
| WO | 00/45706 WO | 8/2000 |
| WO | WO 01/37925 A | 5/2001 |

OTHER PUBLICATIONS

Webster Laboratories, catalog (1991), pp. 60–61.

* cited by examiner

Primary Examiner—Willis R. Wolfe
(74) Attorney, Agent, or Firm—Lerner, David, Littenberg, Krumholz & Mentlik, LLP

(57) ABSTRACT

A treatment catheter (10) carries an elongated ultrasonic emitter (20) extending in the lengthwise direction of the catheter. The array is flexible in all directions transverse to the lengthwise direction. The treatment catheter is inserted into a chamber of the heart and brought to a desired configuration such as a substantially closed loop. The treatment catheter is then biased into engagement with the wall of the heart by an expansible balloon (62) or other expansible structure, which may be carried on a separate stabilizer catheter (60). While the treatment catheter is engaged with the heart wall, the array is actuated to ablate tissue along a path having a shape corresponding to the configuration of the treatment catheter.

60 Claims, 12 Drawing Sheets

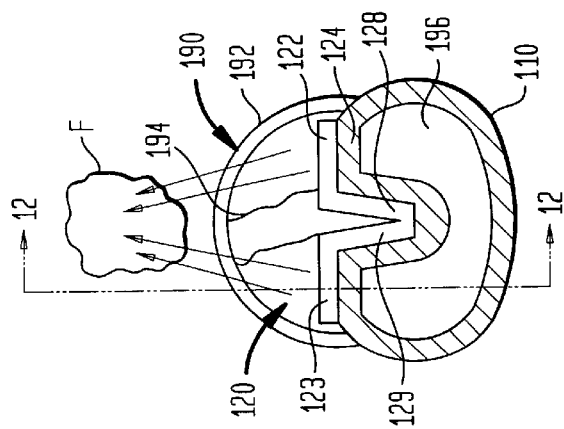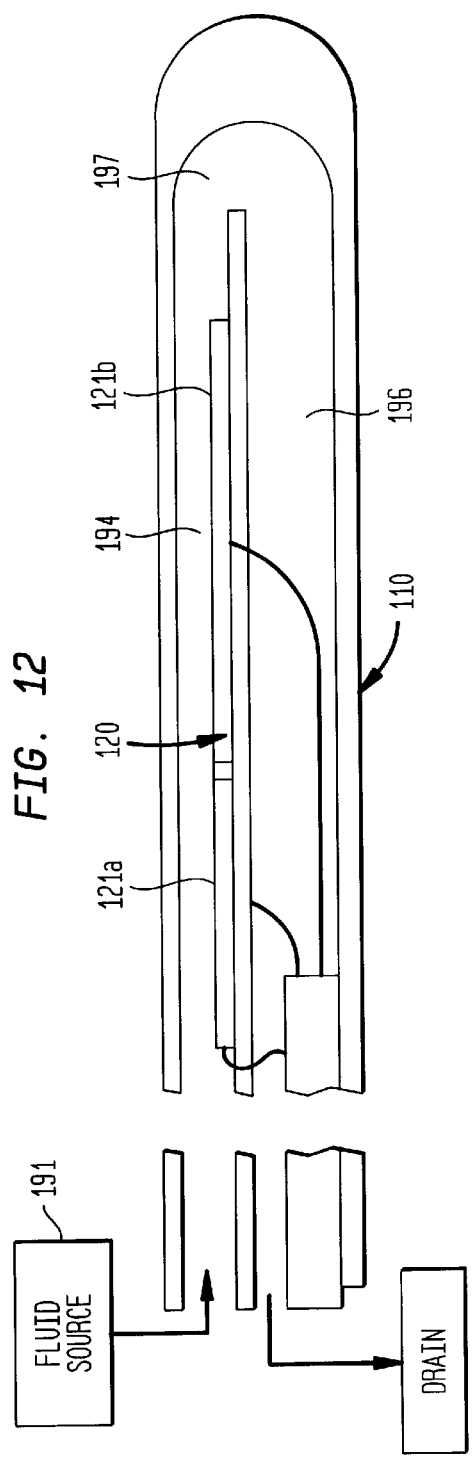

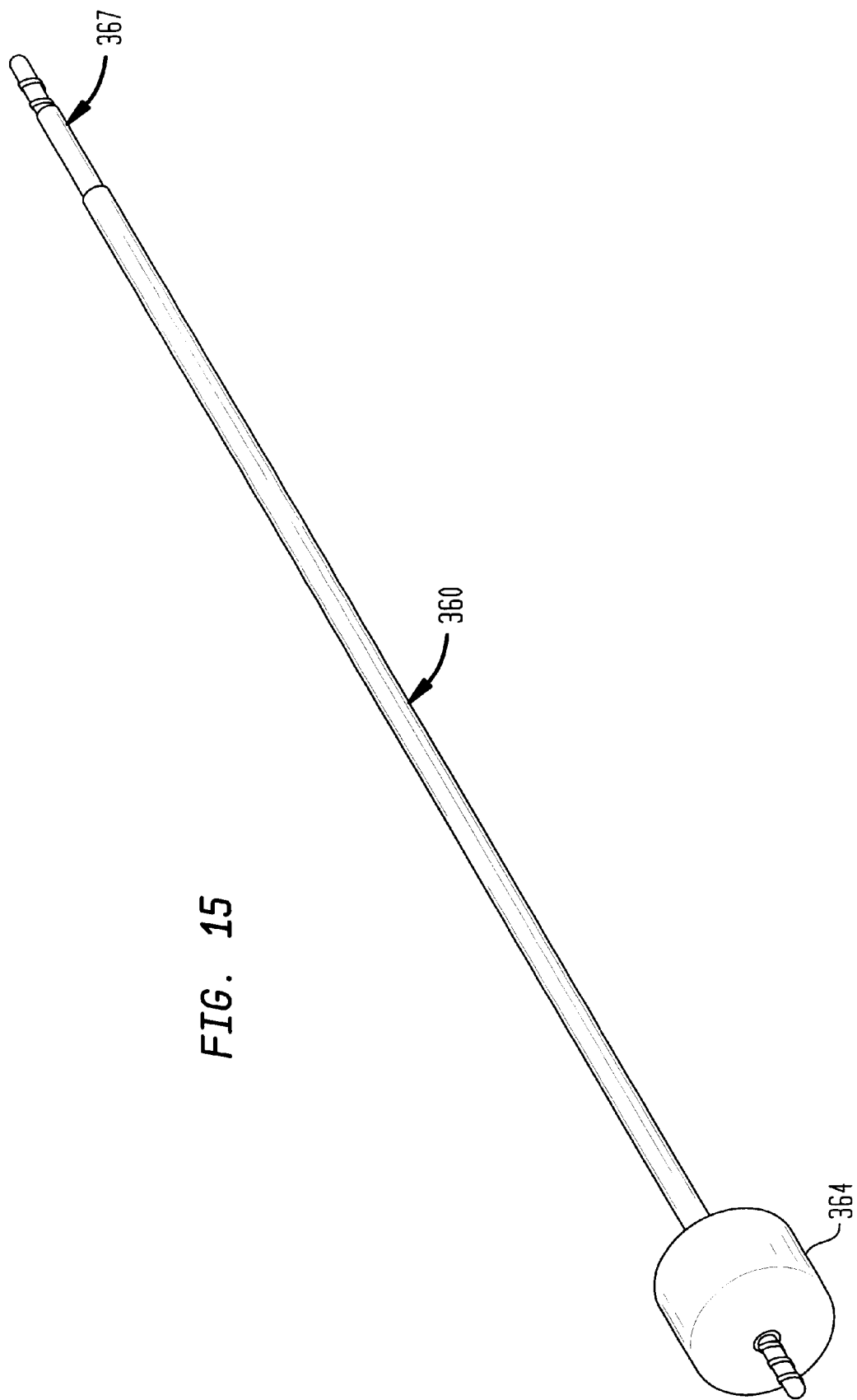

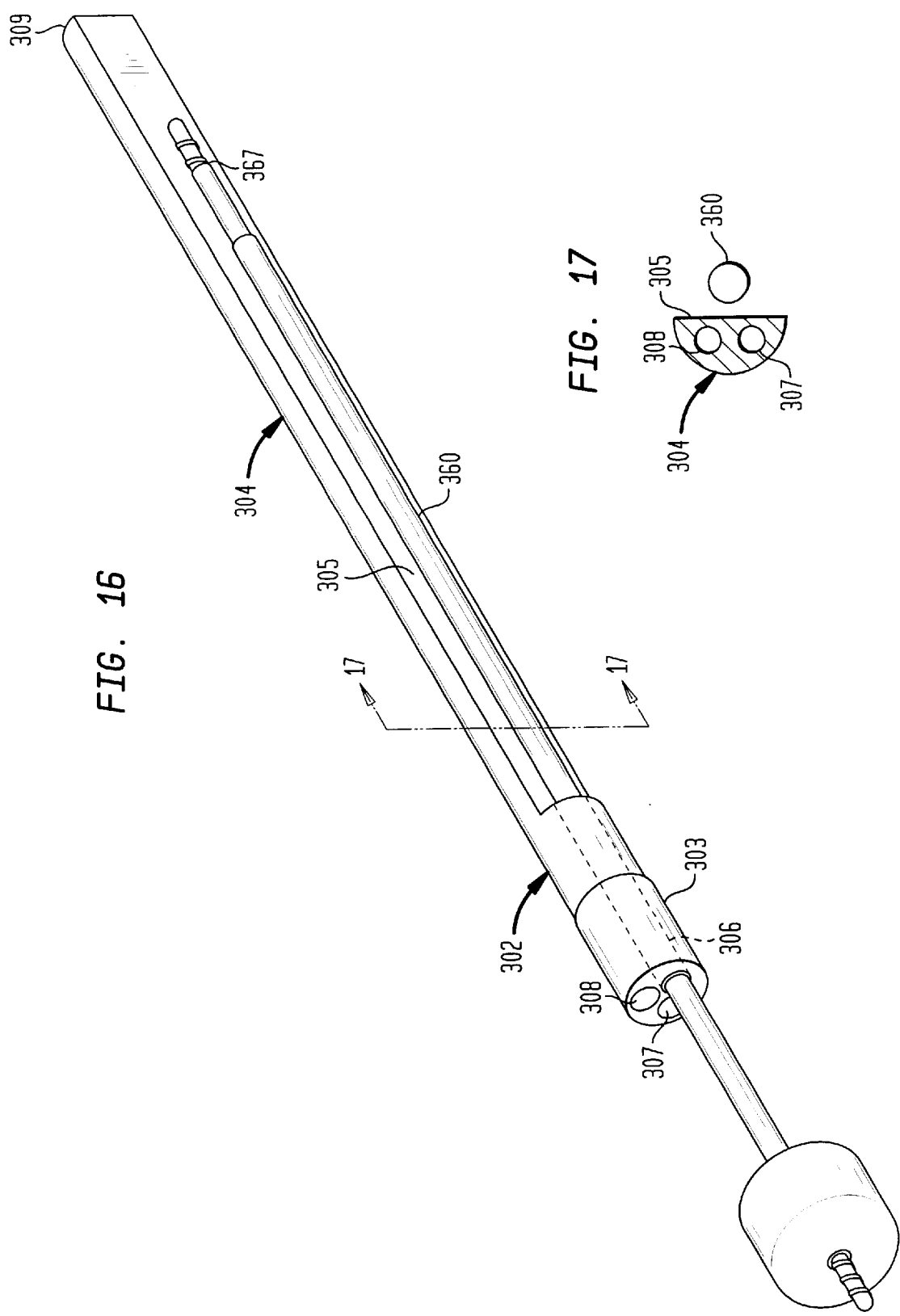

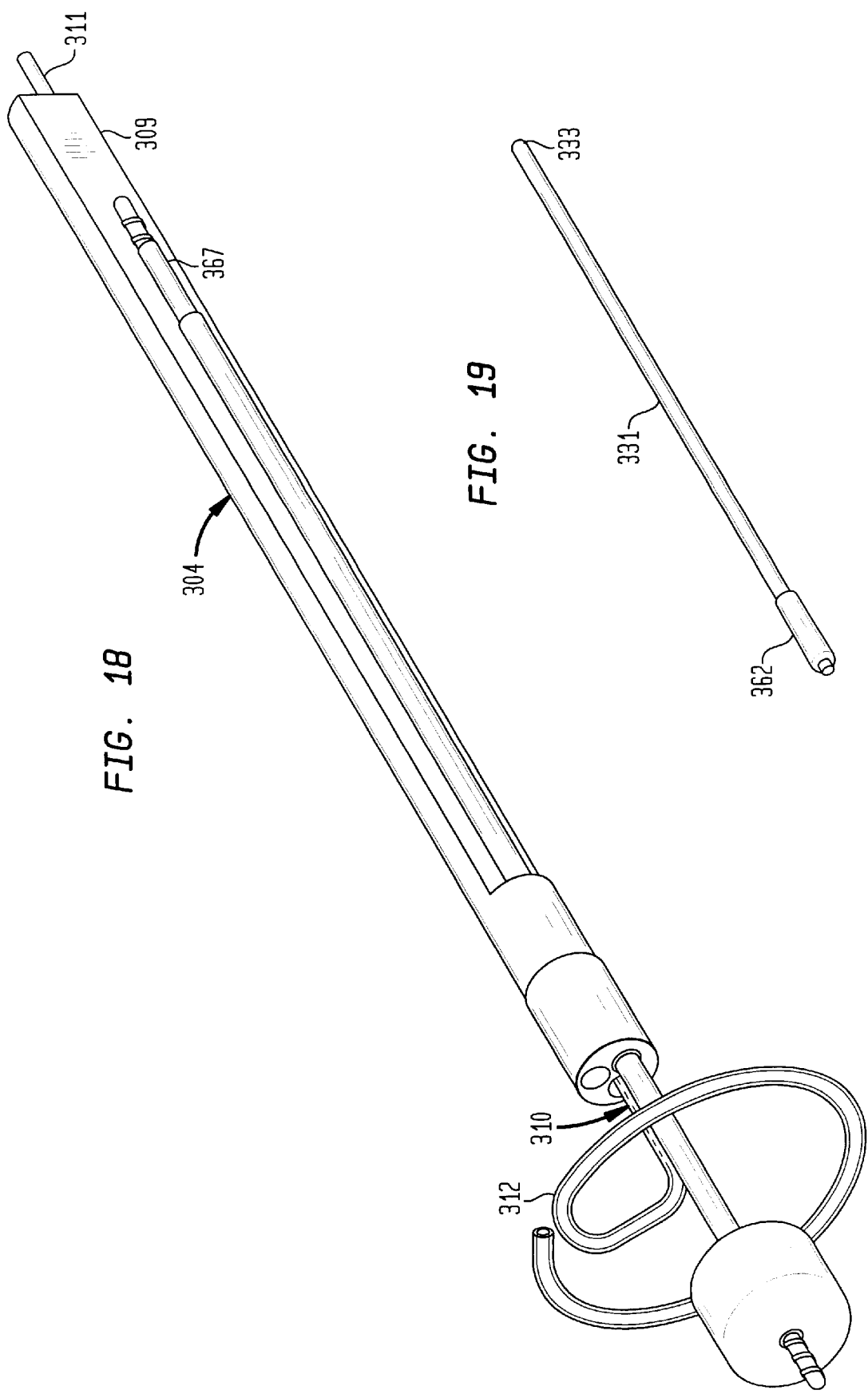

APPARATUS AND METHODS FOR INTRABODY THERMAL TREATMENT

CROSS-REFERENCE TO RELATED APPLICATIONS

The present application claims benefit of U.S. Provisional Patent Application 60/192,074, filed Mar. 24, 2000, the disclosure of which is hereby incorporated by reference herein.

FIELD OF THE INVENTION

The present application relates to medical devices and procedures, and to ultrasonic energy emitters adapted for use in such devices and procedures.

BACKGROUND OF THE INVENTION

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF". Certain cardiac arrhythmias can be treated by deliberately damaging the tissue of the cardiac wall along a path crossing a route of abnormal conduction. This causes formation of a scar extending along the path where disruption occurred. The scar blocks conduction of the electrical impulses. Such a scar can be created by conventional surgery, but this entails all of the risks and expense associated with cardiac surgery. Another approach, described in Swartz et al., U.S. Pat. No. 5,575,766, is to introduce a catheter bearing a localized energy emitter such as an electrode for application of radio frequency ("RF") energy at its distal tip into a heart chamber, such as the right or left atrium of the heart in the case of atrial fibrillation. The physician then moves the catheter so that the tip, and the localized emitter traces the desired path. In AF, the desired path typically is a closed loop encircling the openings or ostia of the pulmonary veins. RF energy applied through the electrode heats the tissue to a degree sufficient to cause death of the normal tissue and its replacement by scar tissue. Heating to this degree is referred to herein as "ablation". The elevated temperature required for ablation varies with the time of exposure to the elevated temperature, but heating to about 60–80° C. is typically used. Tracing a precise path along the interior of a chamber in the heart of a living subject with the tip of a catheter involves inherent practical difficulties. Although curved guide wires can be placed within the catheter so that the catheter tip will tend to follow the guide wire as the physician moves it, the process is still difficult.

Swanson et al., U.S. Pat. No. 5,582,609 describes an elongated catheter having numerous RF electrodes disposed along its length in a distal region adjacent the tip. This distal region can be formed into a curved, looplike configuration and manipulated so that the electrodes lie along the desired path, whereupon RF energy is applied so as to ablate cardiac tissue. In a variant of this approach, the electrodes are mounted on a structure which opens to form a ring-like configuration. Even with these structures, however, it is difficult to assure the desired placement of the RF electrodes. Lesh, U.S. Pat. No. 5,971,983 describes an elongated catheter which is equipped with similar RF electrodes distributed over its distal region, and uses guide wires to position the distal region in place against the wall of the heart. Although this patent mentions a "ultrasonic element such as an ultrasound crystal element" along with numerous other devices as theoretically applicable to cardiac tissue ablation, it offers no structure for an elongated ultrasonic ablating device.

As described in various publications including Swartz, U.S. Pat. No. 5,938,660 and Lesh, International Publication WO 99/02096, the abnormal conduction routes in AF typically extend from the wall of the heart along the pulmonary veins. Therefore, AF can be treated by ablating tissue in a ring around each pulmonary vein at the juncture between the pulmonary vein and the heart. As described in the '096 publication, such ablation can be performed by threading a catheter having a thermal ablation element at its distal tip into the heart so that the tip is lodged within the appropriate pulmonary vein. The catheter may bear a balloon which is inflated within the vein and which holds the catheter in place. The ablating element is then actuated so as to apply heat in a region surrounding the ablating element. In certain embodiments taught in the '096 publication, the ablating element includes a radio frequency ("RF") emitting element which is carried on the surface of the balloon. Ablation of the pulmonary vein using RF energy can create a rough, disrupted surface on the interior of the vein. This or other factors can lead to thrombosis or clot formation.

Other embodiments described in the '096 publication disclose the use of ultrasonic transducers. The preferred ultrasonic transducer illustrated in the '096 publication is a rigid ceramic piezoelectric element disposed on a catheter surrounded by a balloon. When the balloon is inflated, the piezoelectric element remains remote from the wall of the pulmonary vein. The piezoelectric element can be actuated to apply sonic energy through a fluid contained in the balloon, thereby heating the ring of vein wall tissue surrounding the balloon. As a further alternative, the '096 publication shows an ultrasonic emitter in the form of a hollow concave disk. The '096 publication suggests that such an emitter can be physically rotated around the axis of a catheter so as to ablate a ring-like zone. These transducers have numerous drawbacks even for use in ablation of a vein wall and are not adapted for ablation of the wall of the cardiac chamber.

Ultrasonic heating such as high intensity focused ultrasound (HIFU) is utilized for many therapeutic applications. As disclosed in commonly assigned International Application PCT/US98/1062, published as International Publication WO/98/52465 the disclosure which is hereby incorporated by reference herein, HIFU heating typically is conducted using an ultrasonic emitter having an array of transducers. The transducers are actuated with a drive signal so as to emit ultrasonic waves. The relative phasing of the waves is controlled by the physical configuration of the array and the phasing of the drive signal. These factors are selected so that the ultrasonic waves tend to reinforce one another constructively at a focal location. Tissue at the focal location is heated to a greater extent than tissue at other locations. As described, for example in copending, commonly assigned U.S. patent application Ser. No. 09/496,988, filed Feb. 2, 2000 and in the corresponding International application PCT/US00/02644 in copending, commonly assigned U.S. patent application Ser. No. 09/523,614 filed Mar. 22, 2000, and in the corresponding International application PCT/US00/07607 the disclosures of which are also incorporated by reference herein, HIFU may be applied by transducer arrays such as arrays of polymeric piezoelectric transducers. These arrays can be mounted on a probe such as a catheter which can be introduced into the body as, for example, within the vascular system or into a cavernous internal organ. The '988 application discloses certain transducer arrays which can be deformed so as to vary the placement of the focal location.

SUMMARY OF THE INVENTION

One aspect of the invention provides apparatus for applying thermal treatment to tissue of an internal organ of a living subject. Apparatus according to this aspect of the invention desirably includes one or more catheters and an elongated energy emitter carried on one of the one or more catheters. The elongated energy emitter desirably is adapted to assume a desired shape when disposed within the interior of the organ. The apparatus desirably also includes an expansible positioning structure such as a balloon or other expansible element carried on one of the one or more catheters. When the energy emitter is in the desired curved shape, the energy emitter extends over the expansible positioning structure so that the expansible positioning structure can bias the elongated energy emitter against an interior wall of the organ. Thus, when the positioning element and energy emitter are in an operative condition, the energy emitter extends along an elongated path on the interior wall of the organ. The path has a shape corresponding to the desired shape of the energy emitter. The energy emitter desirably is operative to emit energy at a plurality of locations along its length so as to heat tissue surrounding the interior of the organ at a plurality of locations along the path.

Most preferably, the energy emitter is formed separately from the positioning element, so that the energy emitter can assume its desired shape before it is biased against the wall of the organ. The energy emitter may be adapted to assume a curved shape such as a substantially closed loop, so that the path along the interior wall of the organ will be generally in the form of a loop. The energy emitter desirably is adapted to emit energy substantially simultaneously at a plurality of locations along its length to thereby heat tissue at a plurality of locations along the path substantially simultaneously. In a particularly preferred arrangement, the energy emitter is an elongated ultrasonic transducer array.

The one or more catheters desirably include a treatment catheter carrying the energy emitter, the emitter extending lengthwise along the treatment catheter adjacent the distal end thereof. In a particularly preferred arrangement, the energy emitter is an elongated ultrasonic transducer array which is flexible in directions transverse to the lengthwise direction of the catheter to facilitate threading of the catheter into the body. The distal end of the treatment catheter, and hence the energy emitter, may be brought to the desired shape by structures within the catheter, or by additional elements such as curved guide wires or sheaths. The one or more catheters most preferably include a holding structure such as a stabilizer catheter separate from the treatment catheter, the holding structure carrying the expansible positioning element. The apparatus may include an anchor linked to the stabilizer catheter, the anchor being adapted to engage an anatomical structure in or adjacent said organ. The expansible positioning structure may be movable relative to the anchor while the anchor is engaged with said anatomical structure. For example, where the apparatus is used for treatment of atrial fibrillation or other cardiac arrhythmias, the treatment catheter bearing the energy emitter and the stabilizer catheter may be threaded into a chamber of the heart and the treatment catheter may be brought to the desired shape such as a generally loop-like configuration. The expansible positioning structure may be expanded and the anchor may be engaged in a pulmonary vein or other blood vessel, with the treatment catheter disposed between the positioning structure and the wall of the heart chamber. The positioning structure is urged toward the wall of the heart, so as to engage the energy emitter with the wall of the heart, as by moving the stabilizer catheter relative to the anchor. While the energy emitter is engaged with the wall of the heart, it is activated to apply energy and ablate tissue in the heart wall, thereby forming a lesion along a loop-like path. Desirably, the entire lesion can be formed without repositioning or reconfiguring the energy emitter.

A further aspect of the invention provides methods of applying thermal treatment to tissue of an internal organ of a living mammal. A method according to this aspect of the invention desirably includes the steps of inserting an elongated energy emitter into the interior of the internal organ and bringing the energy emitter to a desired shape in a desired position relative to the organ, inserting an expansible positioning element into the interior of the organ, and expanding the positioning structure so that the energy emitter is disposed between the positioning structure and the wall of the organ and the positioning structure biases the energy emitter against the interior wall of the organ. In this condition, the energy emitter extends along an elongated path on such interior wall having a shape corresponding to the desired shape of the energy emitter. While the energy emitter extends along this path, the energy emitter is actuated to emit energy at a plurality of locations along its length so as to heat tissue at a plurality of locations along the path. In a particularly preferred method, the entire lesion is formed in one actuation, or a few actuations, of the energy emitter, without repositioning or reconfiguring the emitter. Most preferably, the energy emitter is brought at least approximately to the desired shape and at least approximately to the desired position before the positioning structure is fully expanded and before the energy emitter is biased against the wall of the internal organ by the positioning element.

In a particularly preferred method, the energy emitter includes an array of one or more ultrasonic transducer elements, the array extending in a lengthwise direction, the one or more transducer elements emitting ultrasonic energy at plural locations along the length of the array. For example, the array may extend lengthwise along a treatment catheter as discussed above in connection with the apparatus. The use of ultrasonic energy allows formation of lesions in the wall with minimal damage to the lining of the wall. In ablation of heart tissue, this minimizes the possibility of thrombus formation. Most desirably, the method includes the step of focusing ultrasonic energy emitted by the one or more transducer elements onto a elongated focal region extending generally parallel to said path. The term "focusing" as used in this disclosure with reference to sonic or ultrasonic energy, refers to providing such energy from spatially-separated regions of a transducer or transducer array such that the ultrasonic waves from plural spatially-separated regions of the transducer or transducer array converge with one another in passing from the transducer or array to a focal region and are in phase within one another within the focal region so that they mutually reinforce one another so as to provide a sonic power density in the focal region higher than the sonic power density at the transducer surface. Most typically, the focal region is disposed on or in the wall of the organ and has an area (measured in a plane normal to the direction of propulsion of the ultrasonic waves) smaller than the area of the transducer. The method may further include the step of varying the focus of the ultrasonic energy so as to move the focal region towards or away from the transducer or array and thereby position said focal region deeper or shallower within the wall of said organ while the array remains substantially in position along the path. The ability to focus the ultrasonic energy allows rapid heating of the tissue, and facilitates heating tissue in the focal region to the extent necessary to ablate it, while minimizing damage to adjacent tissues.

As discussed above in connection with the apparatus, the energy emitter desirably is flexible in directions transverse to its length. The step of inserting the energy emitter may include the step of advancing the array lengthwise through a tubular anatomical structure and then deforming the array in directions transverse to its lengthwise direction to the desired shape.

A further aspect of the invention provides a medical device including an elongated catheter body with proximal and distal directions in its direction of elongation and an elongated ultrasonic transducer array extending in the proximal and distal directions, the catheter body and the transducer array being flexible in all directions transverse to said proximal and distal directions.

Yet another aspect of the invention provides an elongated ultrasonic transducer array having lengthwise directions, the array including a sheetlike element having a first fold extending in the lengthwise directions of the array and defining a first pair of adjacent regions on opposite sides of the fold. These desirably are non-parallel with one another and non-coplanar with one another. For example, the first pair of adjacent regions may define a structure which is generally V-shaped when seen in cross-section with the viewing direction in the lengthwise direction of the array.

Most preferably, at least one of the regions in the first pair is an active region. The array includes a plurality of ultrasonic transducer elements disposed on or formed integrally with the sheetlike element in the active region or regions of such element. The sheetlike element has notches in each of the aforesaid regions, the notches extending along axes transverse to the first fold at locations spaced apart from one another in the lengthwise direction. The notches subdivide each of the regions into panes, the notches in each region of the first pair of adjacent regions being offset in the lengthwise direction of the array from the notches in the other region of such first pair of adjacent regions. Each pane of each region of said first pair has a hinge zone aligned with the axis of a notch in the other region of the first pair. The sheetlike element is flexible at least in the hinge zones. As further discussed below, this arrangement allows the array to bend in directions transverse to said lengthwise direction of the array, and typically allows bending in all directions transverse to the lengthwise direction. The sheetlike element desirably has one or more electrical conductors thereon, the conductors extending lengthwise along the sheetlike element in a zigzag pattern so that the conductors pass through the hinge regions of the panes and around the notches.

Yet another aspect of the invention provides a medical device including an elongated catheter body with proximal and distal directions in its direction of elongation, and an array as discussed above, the lengthwise directions of the array and the first fold extending in the proximal and distal directions of said body. The active region or regions desirably are disposed on or constitute an outwardly-facing surface of said body and extend in lateral directions transverse to said lengthwise directions.

Yet another aspect of the invention provides a medical ultrasonic applicator including a first elongated catheter body having an exterior surface and having proximal and distal directions; a distributed array of one or more ultrasonic transducer elements disposed on or constituting a portion of said exterior surface of said first body, the array extending in the proximal and distal directions; and an elongated lens overlying the array of transducer elements and extending in said proximal and distal directions, said lens being adapted to focus ultrasonic emissions from the transducer elements into a elongated focal region outside of said body but generally parallel thereto. Most preferably, the body, lens and array are flexible in directions transverse to the proximal and distal directions. The lens may include a hollow enclosure extending in the proximal and distal directions, the enclosure being filled with a lens fluid when the device is in an operative condition.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 11 is a diagrammatic sectional view depicting a treatment catheter according to a further embodiment of the invention incorporating the transducer array of FIG. 10.

FIG. 12 is a sectional view taken along line 12—12 in FIG. 11.

FIG. 15 is a view similar to FIG. 14 but depicting the elements in a different operating condition.

FIG. 16 is a diagrammatic perspective view of the elements shown in FIGS. 14 and 15, in conjunction with additional elements of the apparatus.

FIG. 17 is a sectional view taken along line 17—17 in FIG. 16.

FIG. 18 is a diagrammatic perspective view of the elements shown in FIGS. 14–17, in conjunction with additional elements.

FIG. 19 is a diagrammatic perspective view of a stabilizer catheter used with the apparatus of FIGS. 14–18.

DETAILED DESCRIPTION OF THE PREFERRED EMBODIMENTS

One aspect of the present invention provides apparatus for applying thermal treatment such as ablation to tissue in the wall of a cavernous internal organ of a living subject such as a chamber of the heart. Apparatus according to one embodiment of the invention includes a treatment catheter 10 having an elongated body with a distal region 12 adapted to form a desired curved shape when in an operative condition, deployed within a chamber of the heart such as the atrium A schematically shown in FIG. 1. The particular curved shape is generally in the form of a closed or nearly closed loop, as best seen in FIG. 2. The catheter, including distal region 12, should be flexible in directions transverse to the proximal and distal directions, i.e., directions transverse to the lengthwise axis of the catheter, at least during introduction and removal of the catheter.

Figure 3:
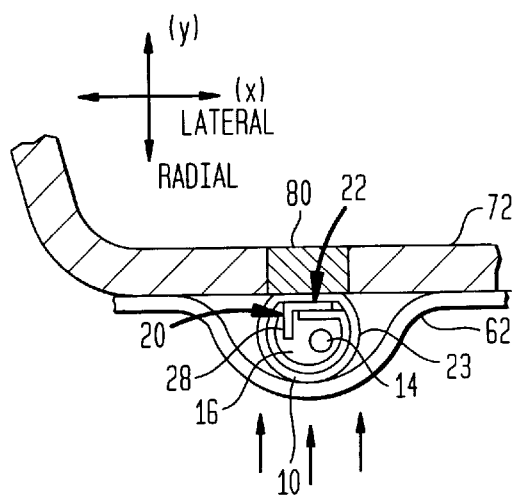
FIG. 3 is a fragmentary sectional view taken along line 3–3 in FIG. 1.

Numerous techniques and structures known in the art for deforming a catheter to a desired curved shape while the catheter is disposed in an internal chamber of the body can be used in the treatment catheter. Merely by way of example, a guide wire which inherently tends to assume such shape, such as a resilient guide wire 14 (FIG. 3) can be provided in the interior bore 16 of the catheter before or after it is deployed. A shape memory alloy guide wire such as a Nitinol (Trademark) wire which is straight at room temperature but which tends to assume the desired curvature at body temperature can be used. The treatment catheter body itself may include these elements, and may be constrained to a relatively straight form during introduction and removal by threading the catheter through a bore of an introducer catheter (not shown). Alternatively or additionally, the treatment catheter may include controllable elements such as steering wires extending through the interior bore for controllably bending the catheter body to the desired shape. In a further alternative, the catheter body may have "dead bend" or non-resilient properties such that once bent to a particular shape, the catheter body retains such shape until it is bent again by external forces. Such a dead-bend treatment catheter can be bent to the preselected shape by the physician after inserting the distal end of the treatment catheter into the heart but before applying energy to ablate tissue as described below.

Treatment catheter 10 has an elongated, flexible ultrasonic transducer array 20 extending lengthwise along the distal region 12 of the catheter body. A signal cable 21 connected to the transducer array extends to the proximal end of the catheter body for connection to an external source of drive signals (not shown). As further discussed below, the elongated transducer array incorporates transducer elements incorporating an electromechanical transduction material, most preferably a polymeric electromechanical transduction material. As used in this disclosure, the term "electromechanical transduction material" means a material which changes dimensions in response to an applied electrical signal. Polymeric electromechanical transduction materials include polymeric piezoelectric materials as, for example polyvinylidene difluoride ("PVDF") and copolymers of PVDF with trifluoroethylene ("PVDF-TrFE"), as well as electrostrictive polymers such as certain silicone polymers. The term "transducer element" as used herein refers to a structure or a region of a structure which is capable of converting a signal in one form to a signal in another form as, for example, a mass or portion of electromechanical transduction material and electrodes juxtaposed with the transduction material. The "transducer array" is used herein as referring to a structure which includes one or more transducer elements. Where a transducer array includes plural transducer elements, these may be connected together, so that the same signal is applied to all of the elements and the plural elements act in much the same way as a single larger element. Alternatively, different elements of a transducer array may be connected to different signal sources as, for example, to sources of signals having preselected phase relationships.

Several conflicting factors complicate the design of an elongated transducer array for ablation along an elongated path within a cavernous organ such as a heart chamber or within the vascular system. These factors include the following:

Diameter: The transducer array must be constructed to fit on a catheters of small diameter. For intracardiac use, the treatment catheter carrying the array should be in the range from 3 French to 12 French catheter size, i.e., about 1 to about 4 mm in diameter.

Flexibility: The necessary flexibility of the particular system will be a function of the target area and the procedure to be employed. For ablating the cardiac wall in a loop surrounding the ostium of a single pulmonary vein in the procedure for treatment of atrial fibrillation depicted in FIG. 1, the minimum radius of curvature that the treatment catheter, and thus the transducer, will have to make is approximately 15–20 mm. Moreover, the transducer array should be flexible in all directions transverse to its direction of elongation to facilitate threading of the treatment catheter through the vascular system and to facilitate intimate engagement of the transducer array and treatment catheter with the cardiac wall.

Power: The required power needed to perform treatment will depend on the specific application. As with most ultrasonic devices, methods to increase output power should be employed, as the higher the power density (emission power per unit surface area), the smaller the device can be and the shorter the treatments become. A transducer array for use in an ablation procedure preferably emits about 5 W/cm$^2$ or more. If the ultrasonic waves from the device are focused into a region smaller than the emitting surface, somewhat lower power density can be employed.

Shielding: The emitter should limit electromagnetic emissions, to avoid interference with other devices used in the hospital environment. For ultrasonic emitters, this typically means the hot electrical leads to the emitter should be shielded to the outside world by grounded layers of conductive material, and that the drive cable should be coaxial, with a grounded outer sheath.

Thermal Control: Ultrasonic emitters, and particularly emitters incorporating a polymeric electromechanical transduction material generate significant heat through dielectric and mechanical losses. The performance (power and frequency) of the device is somewhat a function of the operating temperature. A method of removing heat from the structure should be provided to ensure proper operation of the device (at its tuned frequency and appropriate power levels) as well as to prevent unintended thermal damage to the surrounding tissue as a result of the tissue heating by conduction from hot transducer surface, as opposed to deposition of acoustic power.

Bio-Compatibility: While the primary foreseeable applications of the transducer array will have the transducer positioned inside of an outer sheath or cover, it is still desirable to limit the incorporation of materials which are not approved for patient contact so as to minimize any concerns regarding accidental contact in the event the outer sheath fails during use, and to ease the regulatory process. This factor is more significant if no outer sheath is employed.

Machinability: To make an inexpensive disposable catheter, the transducer array should be designed in such a way so as to take advantage of mass production techniques which can be employed to limit construction costs while maximizing ease of fabrication. Also, the transducer array should include electrical conductors connected to the ultrasonic transducers so as to limit the number of external connections which must be made within the limited space available inside the treatment catheter. This implies that continuous electrical conductors should extend lengthwise along the transducer array. As disclosed in the aforementioned commonly assigned applications, ultrasonic transducer arrays, and particularly ultrasonic transducer arrays incorporating polymeric transduction materials, can be fabricated economically in flat form, using techniques similar to those used in fabrication of printed circuits. It would be desirable to use such techniques in fabrication of an elongated, flexible transducer array. However, printed circuits which incorporate thin, flexible sheetlike materials such as a polyimide dielectric and thin metallic conductors are flexible in only some directions. Such a sheet can bend readily around an axis in the plane of the sheet, but will not bend readily around an axis perpendicular to the plane of the sheet. Thus, a strip of such a sheet will bend readily in a first direction transverse to its length, but will not bend readily in a second direction transverse to the first direction and transverse to the lengthwise direction.

Figure 4:
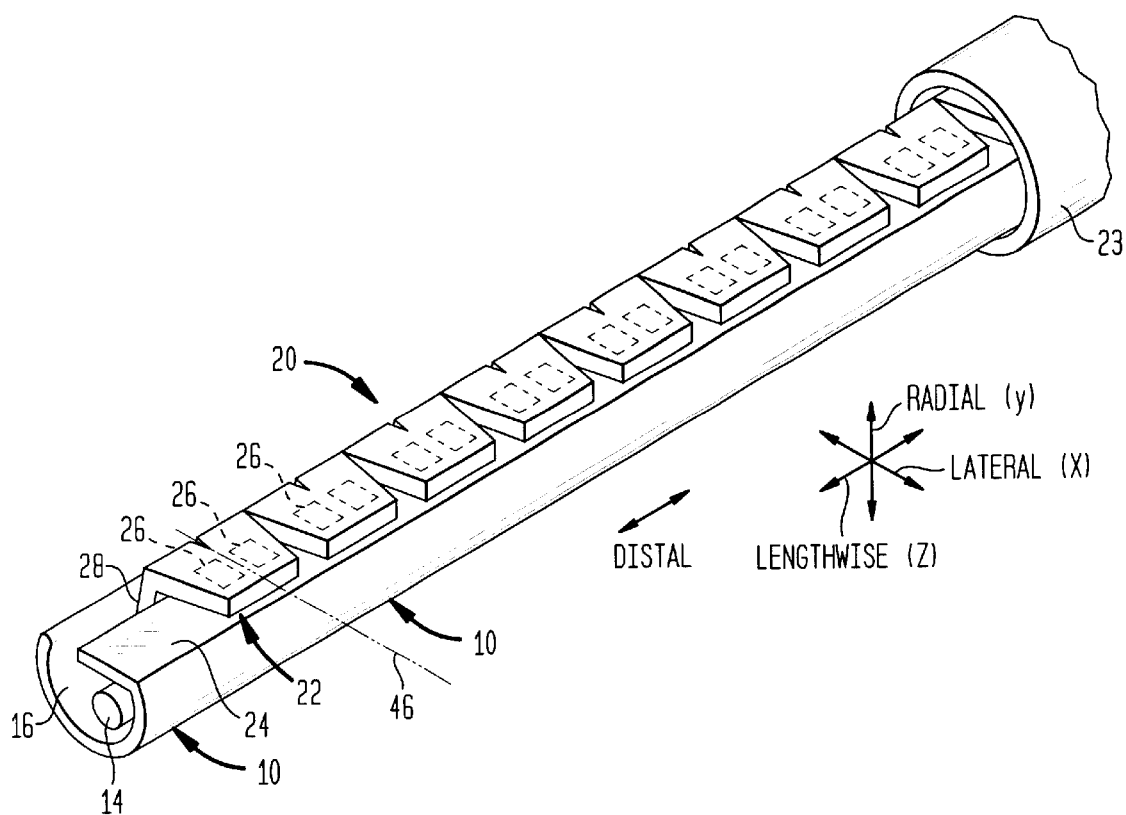
FIG. 4 is a fragmentary, cutaway perspective view of the treatment catheter used in the apparatus of FIGS. 1–3.

The transducer array 20 addresses these factors as further discussed below. The transducer array 20 and its disposition relative to the catheter body are best seen in FIG. 4. Arrows adjacent certain views indicate the directions referred to in the text below. The transducer array has an active region 22 overlying a surface region 24 of the catheter body facing outwardly, away from the interior of the catheter and away from bore 16. In FIG. 4, portions of the active region are omitted for clarity of illustration, to show surface region 24. The active region 22 includes substantially planar transducer elements 26, schematically indicated in broken lines in FIG. 4. The treatment catheter may include a thin outer covering 23, partially cut away in FIG. 4, closely overlying surface region 24 and active region 22 of the transducer array.

The transducer array also includes a radially-extensive additional region 28, also referred to as a back plane region. Region 28 extends inwardly, into the interior of the catheter body and into bore 16. As used in this disclosure, the term "laterally extensive" used with reference to a structural element means that the element extends generally in the lateral direction, and the term "radially extensive" means that the element extends generally in the radial direction, but these terms do not imply that the element extends exactly laterally or exactly radially. Thus, although the particular embodiment illustrated in FIGS. 3–9 has planar regions 24 and 28 perpendicular to one another, these regions need not be exactly planar or exactly perpendicular to one another. Also, the radially-extensive additional or back plane region 28 need not lie exactly on a radial plane of the catheter body.

Figure 5:
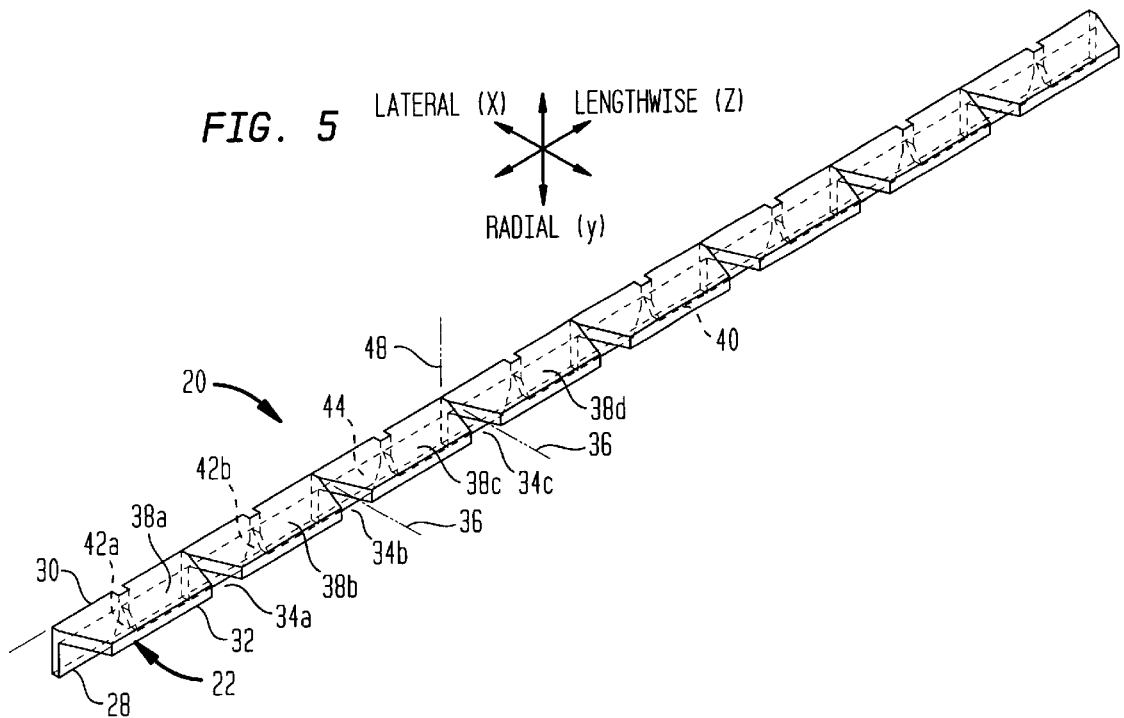
FIG. 5 is a perspective view of an element of the transducer array used in the apparatus of FIGS. 1–4.
Figure 7:
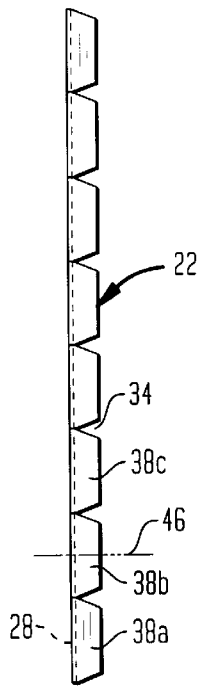
FIG. 7 is a plan view of the transducer array depicted in FIGS. 5 and 6.
Figure 6:
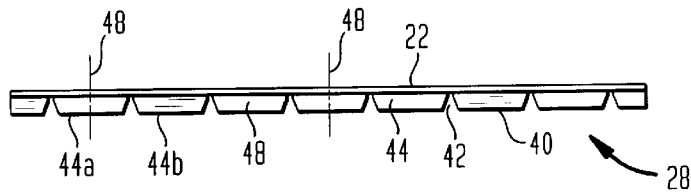
FIG. 6 is an elevational view of the transducer array depicted in FIG. 5.
Figure 8:
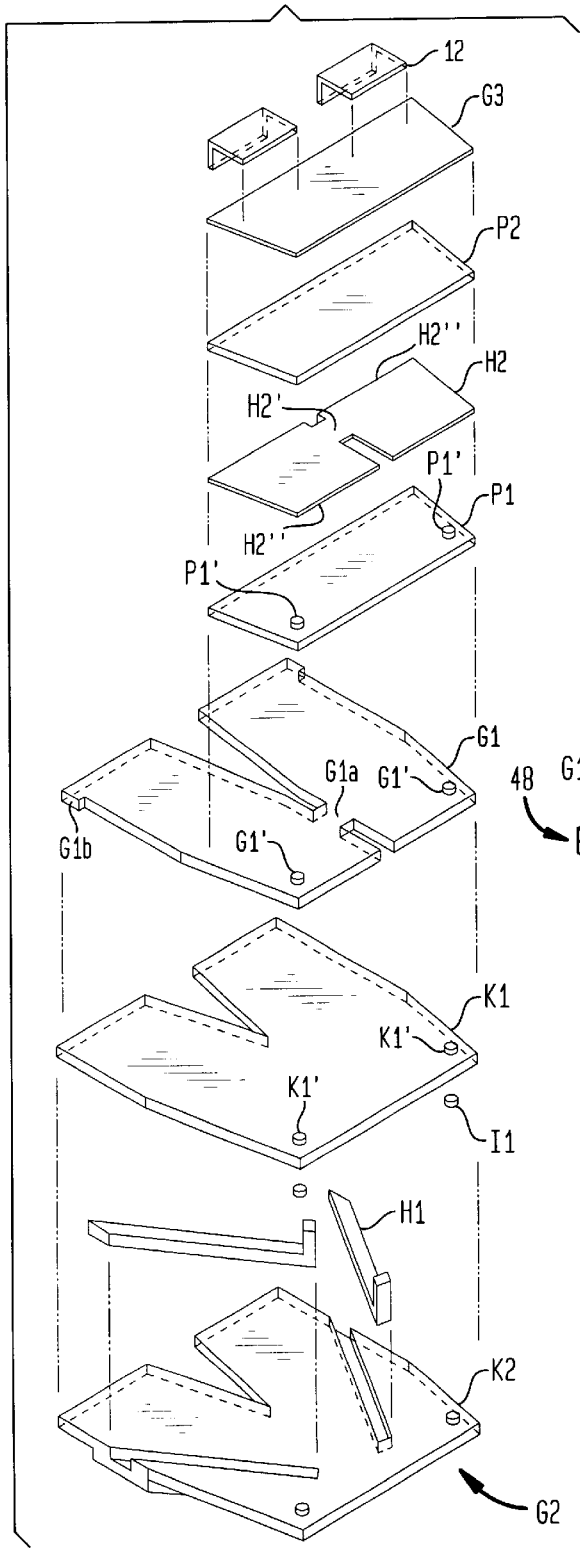
FIG. 8 is an exploded view depicting a portion of the transducer array shown in FIGS. 5–7.

As best seen in FIG. 5, the transducer array 20 is formed as a sheetlike laminate structure generally in the form of a segmented "L" shaped beam. The laminate structure preferably is manufactured flat and folded about a first fold 30 extending in the lengthwise direction of the array. Fold 30 thus subdivides the sheet into the active region 22 and additional region 28, which are non-coplanar and non-parallel to one another. Active region 22 has an outer boundary 32 at an edge of the laminate structure remote from fold 30. Notches 34 extend into active region 22 from its outer boundary 32 along axes 36, generally in the lateral direction transverse to fold 30 and thus transverse to the lengthwise direction of the array. Each notch 34 extends across fold 30 so that a small portion of each notch in the active region extends into the radially-extensive region 28. Each notch 34 is generally triangular, so that the notch is wider at the outer boundary 32 than at fold 30. Notches 34 subdivide the active region into a series of panes 38a, 38b, 38c, and so on.

The radially-extensive additional or back plane region 28 has a similar outer boundary 40 and notches 42 subdividing region 28 into a series of panes 44, seen in broken lines in FIG. 5. Here again, the notches 42 extend transverse to the fold 30 from the outer boundary 40 and slightly across the fold, so that the notches in region 28 extend slightly into active region 22. The notches 42 in region 28 are offset in the lengthwise direction from the notches 34 in region 22, so that each notch 42 in region 28 is aligned with a zone 46 of each panel 38 of region 22. The zone of each panel 38 which is aligned with a notch 46 is referred to as the hinge zone. The hinge zone 46 of panel 38b is indicated schematically by a line in FIG. 5. A single notch 42, with the aligned panel 38 and hinge zone 46 are shown on a larger scale in FIG. 9, in the flat state of the laminate, prior to folding at fold 30. The hinge zone 46 of each panel 38 extends from fold 30 to the outer boundary 32 of region 22. Preferably, each hinge zone 46 lies near the center of the panel in the lengthwise direction. In the same manner, each notch 34 in active region 22 is aligned with a hinge zone of a pane 44 of the additional region 28, one such hinge zone being indicated schematically by a line 48 in FIG. 5.

The array is flexible in hinge zones 46 and 48. The notches and hinge zones permit bending of the transducer array in all directions transverse to the lengthwise direction of the array. Thus, a bend in the YZ plane (in the plane of the radial (Y) and lengthwise (Z) directions) flexes one or more hinge zones 46 in one or more panes 38 of active region 22. Such flexure only requires each hinge zone 46 to bend about a lateral or X-direction line, in the plane of the laminate within the active region, also referred to as "plate mode" bending. As this bending of the radiating plane occurs, the angle between the sides of the notches 42 in additional or back plane region 28 changes. In the same manner, flexure in the XY plane (in the plane of the lateral (X) and lengthwise (Z) directions) flexes one or more hinge zones 48 in the panes 44 of additional or back plane region 28, in a similar plate mode bending action about a line in the plane of additional region 28. Compound bending, with components in both XY and YZ planes is accommodated by a combination of these actions.

Although the structure is free to bend in all directions transverse to the lengthwise direction, the laminate is continuous; it is not separated into isolated pieces by the notches 34 and 42. The laminate therefore can accommodate continuous electrical conductors (further discussed below) extending in the lengthwise direction; these conductors extend around the notches, so that each conductor runs in part on a pane 38 of the active region, then runs on a pane 44 of the additional or back plane region 28 past a notch 34 in the active region, and then runs on a pane 38 of the active region past a notch 42 in the back plane region, and so on.

As shown in FIG. 4, the hinge zone 46 of each panel 38 lies between zones of the panel constituting the active transducer elements 24. Panes 38 need not be, and preferably are not, flexible in the regions constituting the transducer elements. The two zones of each pane 38 constituting the transducer elements 24 are kept rigid and the bend is confined to the hinge zone 46 by a patterned metallic ground/acoustic reflecting layer, further discussed below. Likewise, a localized hinge is built into each panel 44 of the back plane region 28 by controlling the location of the metallic traces on panel 44.

Figure 9:
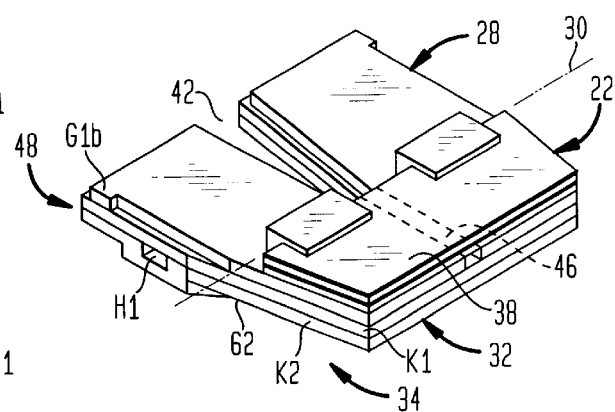
FIG. 9 is a fragmentary, cutaway perspective view depicting a portion of the transducer array shown in FIGS. 5–8.

The laminate is formed as a multi-layer flex circuit. One example of a multilayer construction which provides the features discussed above is shown in FIGS. 8 and 9. A lower dielectric layer K2 is formed from a polymeric dielectric such as 1 mil (25 μm) thick Kapton (trademark) polyimide. A conductive lower shield ground G2, which may be a thin sputtered layer of copper or other metal, lies on the bottom surface of layer K2. In the assembled catheter, this layer is connected to the coaxial shield of the signal cable within the lumen of the catheter. A lower hot lead H1 runs on the upper surface of dielectric layer K2, so that layer K2 separates the lower G2 shield ground from lower hot lead H1. As best seen in FIG. 9, layer K2 may have a depression in its upper surface to accommodate hot lead H1. An main or upper dielectric layer K1, also formed from a 1 mil polyimide, overlies H1 and K2. Layer K1 has vias K1' extending through it.

A ground layer G1 overlies dielectric K1. Layer G1 is formed from a metal such as copper. The thickness of the copper layer is selected to optimize its acoustic reflecting properties. This layer forms both a ground electrode and an acoustic reflecting layer for the transducer elements. Layer G1 has holes G1' aligned with vias K1. Layer G1 has narrow regions G1a in the areas which will form the hinge zones 46 of the active region, and has narrow regions G1b in the areas which will form the hinge zones of the back plane region 28.

Lower active polymer layer P1, formed from a polymeric piezoelectric material such as PVDF-TrFE, with a frequency selected to optimize its response at the desired emission frequency, overlies layer G1 in the active region 22, and has vias P1' aligned with vias K1' and holes G1'. A conductive hot electrode layer H2 overlies layer P1 and a further active polymer layer P2 overlies layer H2. Layer H2 may be formed as a sputtered coating on the bottom surface of layer P2. Layer H2 has a narrow neck H2' at the hinge region 46, and two wide regions H2" on opposite sides of the neck, in those regions which will constitute active ultrasonic emitting transducer elements. A top ground layer G3, such as a sputtered conductive coating, overlies layer P2. Conductive tabs I2, which may be formed from a material such as silver epoxy connect ground layers GI and G3.

The lower hot lead H1 extends into the additional or back plane region 28 (FIG. 9) of the laminate, and extends past notches 34 between panes of the active region 22. Within the panes of the active region, the lower hot lead H1 is interrupted at the hinge region 46. Each portion of H1 extends upwardly through a via K1' and through the corresponding hole G1'. Silver ink pads I1 may be provided at the vias to ensure contact between H1 and H2. However, H1 does not make contact with G1. H1 and H2 thus constitute a continuous "hot" or signal conductor extending lengthwise along the transducer array, but alternately running on the active region 22 and on additional or back plane region 28. Ground layer G1 provides a similar ground conductor.

As best seen in FIG. 9, the neck region G1b and hot lead H1 are offset from one another in the direction towards and away from fold 30 within each hinge zone 48 of the back plane region 28, which enhances flexibility at the hinge zone. The neck regions H2' and G1a (FIG. 8) are similarly offset from one another in the direction towards and away from fold 30 within each hinge zone 46 of active region 22.

Figure 1:
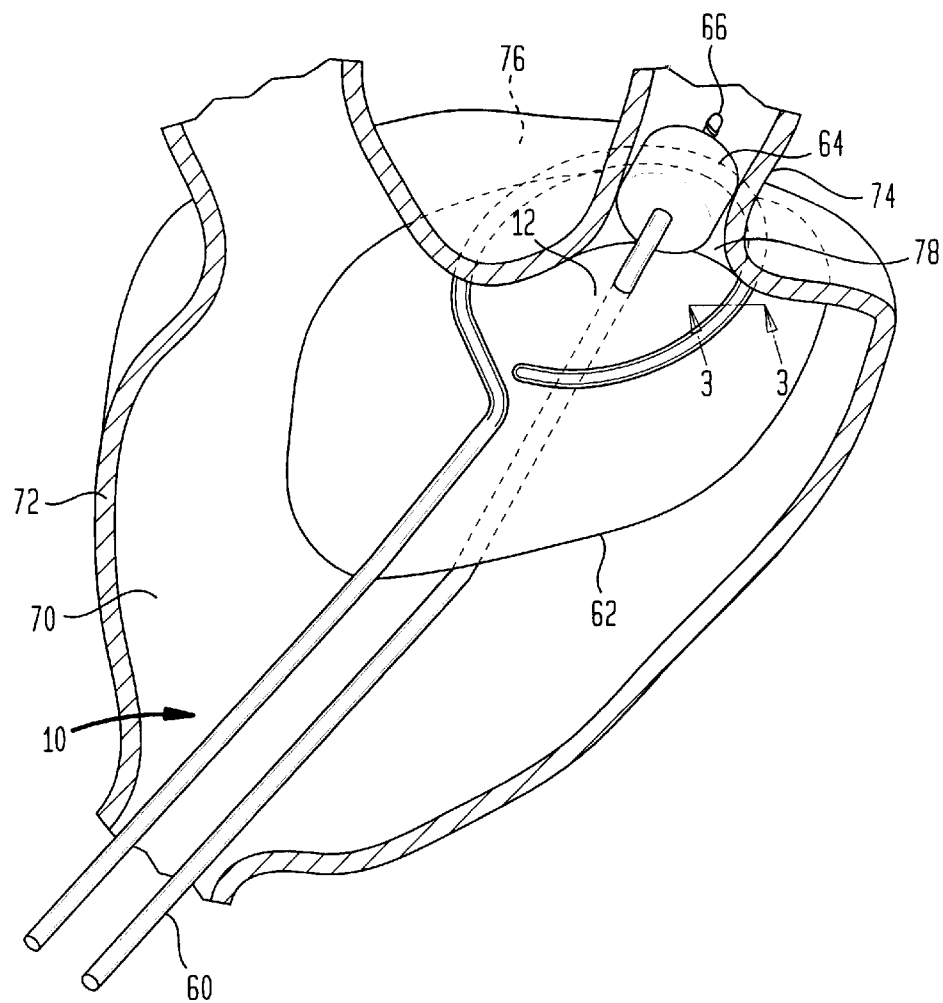
FIG. 1 is a diagrammatic, cutaway perspective view depicting apparatus according to one embodiment of the invention during use.
Figure 2:
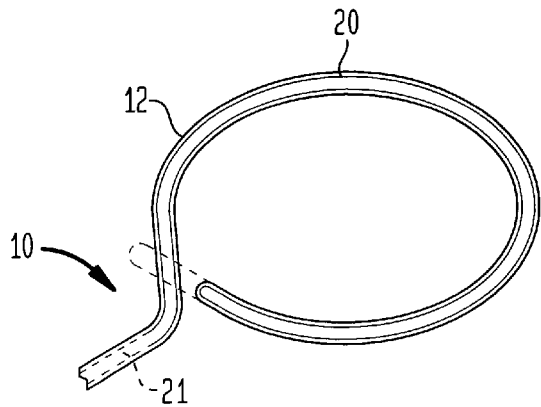
FIG. 2 is a fragmentary, diagrammatic perspective view of a treatment catheter used in the apparatus of FIG. 1.

The apparatus further includes a holding structure including a stabilizer catheter 60 (FIG. 1). The holding structure further includes an expansible positioning element in the form of a balloon 62 disposed adjacent the distal end of the stabilizer catheter. A lumen (not shown) communicating with the interior of balloon extends to the proximal end of the stabilizer catheter. The stabilizer catheter optionally has an expansible anchor in the form of a further balloon 64 disposed between positioning element 62 and the distal tip 66 of the stabilizer catheter, and a further lumen (not shown) is provided in the stabilizer catheter for inflation and deflation of the anchor balloon.

In a method according to one embodiment of the invention, the distal region 12 of treatment catheter 10 is advanced through the vascular system and into a chamber of the heart, such as an atrium 70 of the subject's heart. The distal portion of stabilizer catheter 60 is also threaded into the atrium and into a pulmonary vein 74 so that the expansible positioning element or balloon 62 lies within the atrium and so that the tip 66 and anchor balloon 64 lie within the pulmonary vein. The threading operation may be performed by conventional techniques, using conventional expedients such as guide wires and introducer catheters. The two catheters may be threaded simultaneously or sequentially. The distal region 12 of the treatment catheter, and hence transducer 20, are brought to the desired curved shape and positioned against the interior surface of the wall 72 of the atrium so that the distal region of the catheter and the transducer array 20 extend along the desired path 76 on the interior surface of wall 72, with the active region 22 of the transducer facing the wall surface. For treatment of atrial fibrillation, this path may encircle the ostium (opening) 78 of a pulmonary vein. The proper shape and positioning of the treatment catheter and transducer relative to the heart may be confirmed by imaging such as fluoroscopy, X-ray, CAT, MRI or other conventional imaging techniques, or by means of position sensors (not shown) in the treatment catheter. Such position sensors may include magnetic or radio frequency transmitters or receivers disposed along the distal region. Using known techniques, the location of each sensor can be determined in a sensing frame of reference, and this position can be correlated to the frame of reference of a preexisting image.

After the treatment catheter has been brought to the desired shape and position, positioning element or balloon 62 is expanded within the atrium so that the balloon urges the treatment catheter 10 and transducer array 20 into engagement with the wall 72 of the atrium. Before or during this step, anchor 64 may be expanded to hold the stabilizer catheter in place. Alternatively, if anchor 64 is omitted or is not inflated, the physician can hold the proximal end of the stabilizer catheter against movement in the proximal direction. Other techniques, such as an anchor in the vascular system proximal to balloon 62 or outside of the patient's body may be used to hold the stabilizer catheter in place. The positioning element or balloon holds the treatment catheter and transducer array in place with a substantially uniform pressure over the entire path 76.

While the treatment catheter is engaged in this manner, the transducer array is actuated by applying an electrical signal through cable 21 of the treatment catheter at an appropriate ultrasonic frequency such as 1–5 MHz or higher. The signal voltage is applied to hot layer H2 (FIG. 8) causing piezoelectric layers P2 and P1 within each transducer element 26 to expand and contract in the direction normal to the plane of the active region 22, so that the transducer elements emit ultrasonic waves. These waves are absorbed by the tissue of wall 74 overlying the active region, so that the tissue within a treated region 80, extending through wall 74 on path 76 is ablated to form a scar or conduction block. The catheters are then removed.

Figure 10:
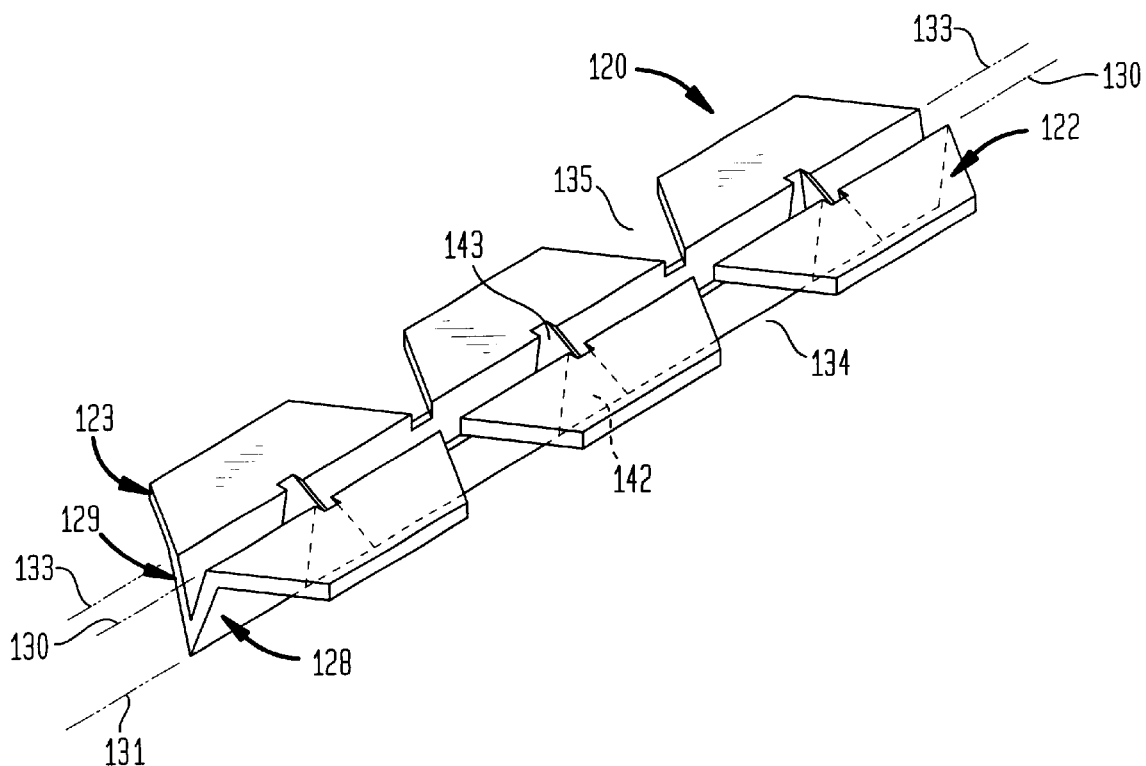
FIG. 10 is a fragmentary, diagrammatic perspective view depicting a transducer array according to a further embodiment of the invention.

A transducer array according to a further embodiment of the invention (FIG. 10) includes three folds 130, 131 and 133 extending lengthwise along the array and generally parallel to one another. First fold 130 lies between a first active region 122 and a first additional region 128. These regions constitute a first pair of adjacent regions, and may be configured in essentially the same way as regions 22 and 28 discussed above. For example, the notches 142 dividing the first additional region 128 are offset in the lengthwise direction of the array from the notches 134 in the first active region. Second fold 131 lies between the first additional region 128 and the second additional region 129, whereas the third fold 133 lies between the second additional region 129 and a second active region 123. Regions 123 and 129 form a second pair of adjacent but non-coplanar regions. This pair can also be similar to regions 22 and 28 discussed above. Here again, each of the regions is subdivided into panes by notches, and notches 143 of the second additional region 129 are offset in the lengthwise direction from the notches 135 in the second active region 123. In this embodiment, the second fold 131 constitutes the outer boundaries of regions 128 and 129, i.e., the boundaries of those regions remote from first fold 130 and third fold 133, respectively. The two additional regions 128 and 129 may lie in planes which are parallel or nearly parallel to one another. The notches 142 and 143 in the additional regions are aligned with one another in the lengthwise direction of the array. Likewise, the notches 134 and 135 in the active regions are aligned with one another. This arrangement also provides flexibility in all directions transverse to the lengthwise direction.

The treatment catheter shown in cross-section in FIGS. 11 and 12 includes a transducer array 120 as, for example, a transducer array as discussed above with reference to FIG. 10. Active regions 122 and 123 of the transducer array are disposed on an outwardly-facing surface portion 124 of the catheter body. The treatment catheter further includes a lens 190 overlying the transducers. Lens 190 extends lengthwise along the treatment catheter. The treatment catheter, lens and transducer array are flexible in directions transverse to the lengthwise or proximal to distal direction of the catheter. In this embodiment, the lens is formed by a hollow enclosure 192 defining a lumen 194 which may be filled with a fluid referred to herein as the lens fluid such as a dense fluorinated fluid of the type sold under the trademark Fluorinert. The lens serves to refract the ultrasonic waves from the transducers so that they constructively reinforce one another in an elongated focal region F outside of the catheter body but extending generally parallel to it.

The lens fluid should have an acoustic velocity different from the acoustic velocity in water, so that the ultrasonic waves will be refracted at the interface between the lens and the surrounding tissue of the body. However, the acoustic impedance of the lens fluid should be close to that of water, to minimize reflection at the interface. The focused waves provide rapid heating within the focal region. By varying the pressure of the lens fluid, the shape of the lens can be varied so as to vary the refractive properties of the lens and move the focal region towards or away from the catheter. The focal region can be moved while the treatment catheter and transducer array remain in place along the desired path. The lens fluid may also act as an imaging marker to render the treatment catheter more visible in an imaging procedure. For example, where X-ray procedures such as fluoroscopy or CAT imaging are used, the lens fluid may be radioopaque. Where magnetic resonance imaging is used, the lens fluid may include a substance with magnetic resonance properties distinct from those of the surrounding tissue to enhance visibility of the treatment catheter in a magnetic resonance image. Fluids having such distinct magnetic resonance properties may include substances such as paramagnetic ions, as, for example, transition metal cations (e.g., $Gd^{+3}$, $V^{+4}$, $V^{+3}$). In a further alternative, the lumen used to hold the lens fluid may be filled with a fluid which acts as a marker during imaging and the same lumen may be filled with another fluid more suitable for use as a lens during operation of the transducer array. In a further variant, the refractive properties of the lens can be varied so as to move the focal region by replacing the lens fluid with a different lens fluid. Where the fluid in the lens lumen is to be varied during the course of the procedure, the lens lumen 194 optionally may communicate with another lumen 196 on the interior of the catheter body at an opening 197 disposed distally of the transducer array 120 so that fluid can be passed into the lens lumen from a source 191 connected at the proximal end of the catheter, pass through the lens lumen 194 and pass into lumen 196, where it is conducted to the proximal end of the catheter and out to a drain 193 or back to source 191. Such an arrangement can be used to assure bubble-free filling of the lens lumen. Moreover, circulation can be maintained during operation, so that the circulating fluid helps to conduct heat from the transducer array. Flow can be provided either continuously or intermittently. The reverse flow (through lumen 196 to opening 197 and back out through lens lumen 194) can be used.

In a further variant, the lens lumen can be pre-filled with a bubble-free fluid before use, desirably during manufacture. The treatment catheter may be maintained in a substantially gas-impermeable wrapper which may have its interior at vacuum to maintain the lens fluid bubble-free after manufacture but before use. The gas-impermeable wrapping may also serve as a sterility-preserving package.

Array 120 is electrically connected as two separate subarrays 121a forming the proximal portion of the array and 121b forming the distal portion of the array. The subarrays are connected to separate signal leads 127a and 127b, respectively, in the signal cable so that the transducer elements in each subarray can be excited independently. This allows operation of the array to treat tissue overlying different portions of the treatment catheter at different times and/or at different intensities. The ground connections of the subarrays may be common.

Figure 13:
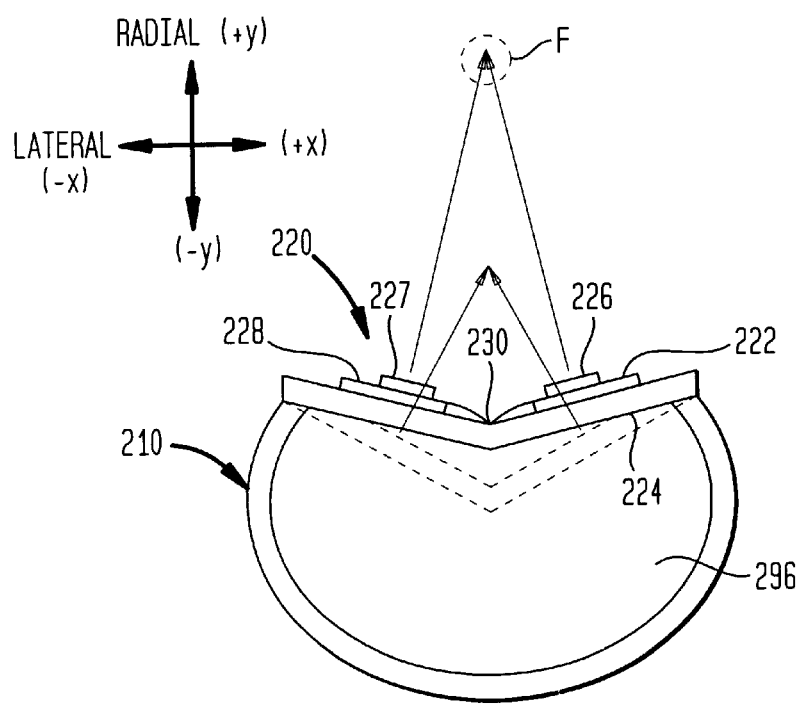
FIG. 13 is a sectional view depicting a treatment catheter according to a further embodiment of the invention.

The treatment catheter 210 seen in cross-section in FIG. 13 includes a transducer array 220 which, like the arrays discussed above, has a lengthwise fold 230 (seen in end view) subdividing the sheetlike element forming the array into two non-coplanar regions 222 and 228. In this array, however, both regions are active, and both include transducer elements 226 and 227. The regions 222 and 228 desirably include notches (not shown) similar to the notches discussed above with reference to FIGS. 1–9, subdividing each region into panes. Here again, the notches in each region desirably are offset from the notches in the adjacent region, so that a notch in one region is aligned with a hinge zone of a pane in the adjacent region to provide multidirectional flexibility. The array as seen in cross-section is generally V-shaped. Thus, region 222 and planar transducer elements 226 on that region slope radially outwardly, away from the center of the catheter body (in the +Y direction, toward the top of the drawing in FIG. 12) in a first or +X lateral direction (to the right in FIG. 13). Region 228 and transducers 227 slope laterally outwardly (in the +Y direction) in the opposite or X lateral direction (to the left in FIG. 13). Thus, the transducers are aimed along converging directions, towards an elongated focal region F outside of the catheter body but parallel thereto. The treatment catheter body defines a lumen 296. By varying the pressure of the fluid in lumen 296 to deform the catheter wall 224, the angle between regions 222 and 228 at fold 230 may be varied, as shown in broken lines, so as to the vary the position of the focal region.

The approaches shown in FIGS. 11 and 12 may be combined. Thus, by varying the pressure of a fluid in the lumen 196 of the treatment catheter relative to the pressure of the lens fluid in lumen 194, the wall of the treatment catheter can be deformed so as to tilt active regions 122 and 123 relative to one another. In such an arrangement, the port 197 shown in FIG. 12 would be omitted or equipped with a valve (not shown) to permit maintenance of different pressures in the two lumens 194 and 196 of the catheter.

In the discussion above, the sheetlike structure forming the transducer array is referred to as having one or more folds. The term "fold" as used herein should be understood broadly as including a crease or juncture between regions of a sheetlike element extending in different planes or tangent to different planes. Thus, although structures incorporating folds are most preferably formed by making the structure in planar form and then deforming it to form the fold, this is not essential. For example, the folded structures discussed above can be formed by fabricating a backing element with a fold, such as by extruding a polymeric structure with an L-shaped or V-shaped cross-section, and forming transducer elements in place on the preexisting folded structure.

Also, although the elements constituting the transducer array have been described separately from the structure of the catheter carrying the array, this is not essential. Thus, the structures constituting the transducer array can also form portions of the catheter walls. The polymeric electromechanical transduction material can form part of the catheter wall, or can be applied as a coating thereon. Where "poling" or exposure to high electric fields under controlled conditions is required to impart piezoelectric properties to a polymer, this procedure can be performed with the polymer in place on, or as part of, the catheter. Electrodes and/or backing elements in the transducer structure can be fabricated by depositing metals or other suitable materials on the catheter wall itself.

Apparatus according to a further embodiment of the invention, shown in FIGS. 14–20 includes a treatment catheter 310 (FIG. 18) similar to those discussed above, having a distal region 312 bearing an elongated transducer array. The apparatus further includes a stabilizer catheter 360 (FIG. 14) having an internal guide wire 361, which may be permanently installed within the stabilizer catheter or which may be removable. The stabilizer catheter has an expansible anchor in the form of a balloon 364 disposed adjacent its distal end.

The apparatus further includes a delivery system catheter 302 having a head 303 at its distal end and a main portion 304 extending from the proximal side of the head to the proximal end of the delivery system catheter. Head 303 is generally cylindrical, whereas main portion 304 has the shape of a cylinder with a sector removed (FIG. 17) so as to define a face 305 recessed radially relative to the head 303. The delivery system catheter has a stabilizer lumen 306 aligned with the recess in main portion 304 and extending through the head 303. The delivery system catheter 302 also has a treatment catheter lumen 307 and pusher catheter lumen 308 extending through the head 303 and through the main portion 304 to the proximal end 309 of the main portion.

A pusher catheter 331 has an elongated body and an expansible positioning balloon 362 mounted adjacent the distal end of such body. The pusher catheter has an internal lumen (not shown) for inflation and deflation of balloon 362.

Figure 14:
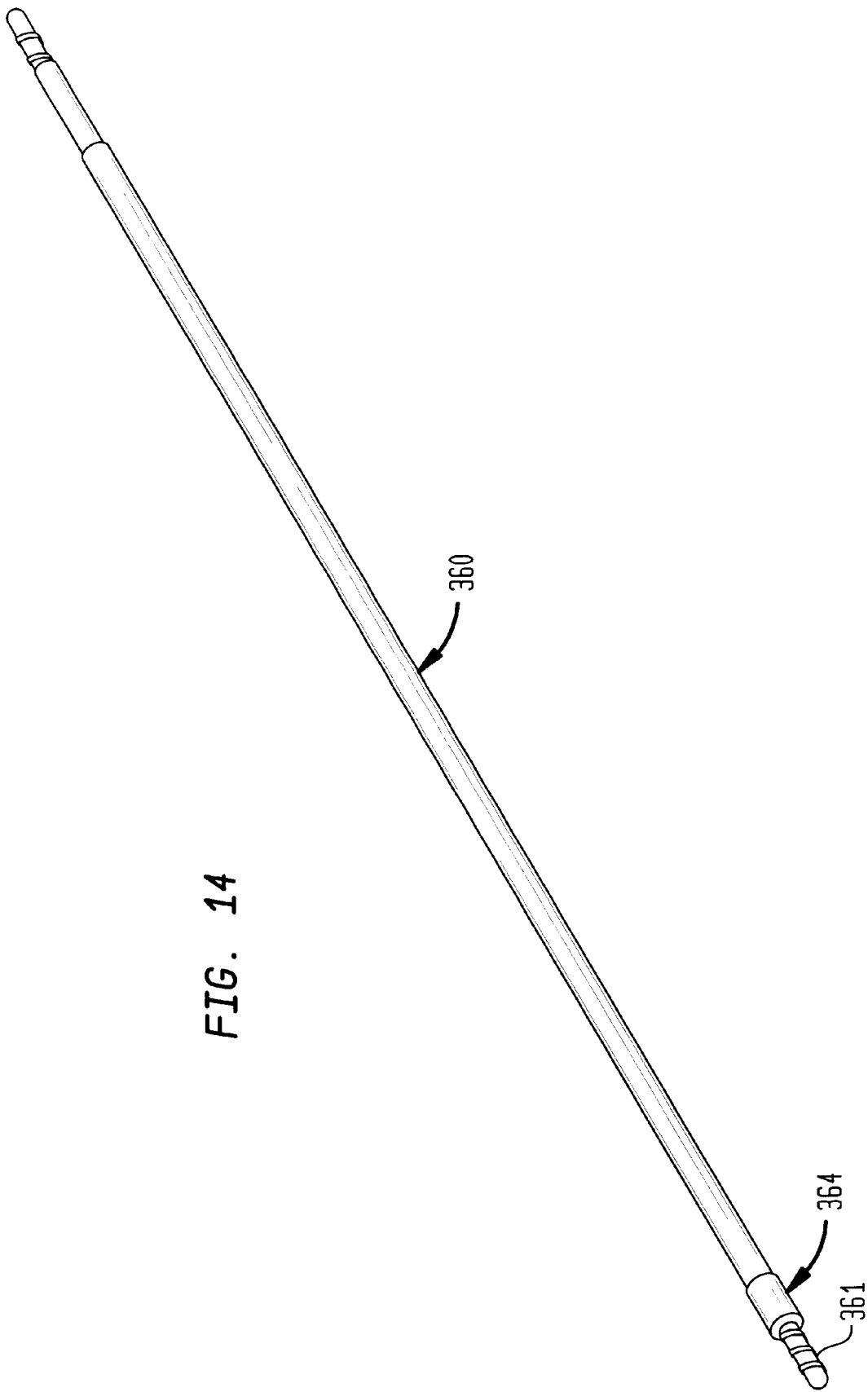
FIG. 14 is a diagrammatic perspective view depicting elements of apparatus according to yet another embodiment of the invention.

In use, the stabilizer catheter 360 is advanced through the vascular system with anchor 364 in the collapsed condition illustrated in FIG. 14, until the anchor is disposed within a pulmonary vein. The anchor balloon 364 is expanded as depicted in FIG. 15 to anchor the stabilizer catheter in place. The proximal end 367 of the stabilizer catheter remains accessible, desirably outside of the body of the patient.

With the stabilizer catheter and anchor balloon in place, the proximal end 367 of the stabilizer catheter is threaded through the stabilizer catheter lumen 303 of delivery system catheter 302. An appropriate guide or threading aid (not shown) may be used to facilitate this procedure. Alternatively, the proximal end of the stabilizer catheter may be threaded into the lumen 303 of the delivery system catheter before the stabilizer catheter is advanced into the subject. The delivery system catheter is then advanced along the stabilizer catheter until head 303 is disposed in or near the chamber of the heart to be treated. The stabilizer catheter guides the delivery system catheter during its advancement. The stabilizer catheter 360 lies within the recess defined by the main portion 304 of the delivery system catheter, alongside face 305 (FIG. 17).

After the delivery system catheter is in place, the treatment catheter is advanced through the treatment catheter lumen 307 of the delivery system catheter and the distal region 312 of the treatment catheter is brought to the desired shape (FIG. 18) and positioned within the heart chamber in the correct location. In this condition, the proximal end 311 of the treatment catheter remains accessible at the proximal end 309 of the delivery system catheter 304. Even if the distal region 12 of the treatment catheter is resilient and hence tends to deform to the desired shape during the threading process, the delivery system catheter confines the distal region to a substantially straight condition during threading and facilitates the threading process. The delivery system catheter desirably has a smooth, low-friction surface on the interior of lumen 307. The interior of the lumen, the exterior of the treatment catheter or both may be lubricated to further facilitate threading.

Pusher catheter 331 is threaded through the pusher catheter lumen 308 of the delivery system catheter until the expansible positioning element 362 passes out of the distal end of the delivery system catheter and into the heart chamber. The proximal end 333 of the pusher catheter remains accessible at the proximal end 309 of the delivery system catheter. The delivery system catheter guides the pusher catheter and facilitates the threading operation. Preferably, the pusher catheter is threaded after the treatment catheter is in place and in the desired shape.

Figure 20:
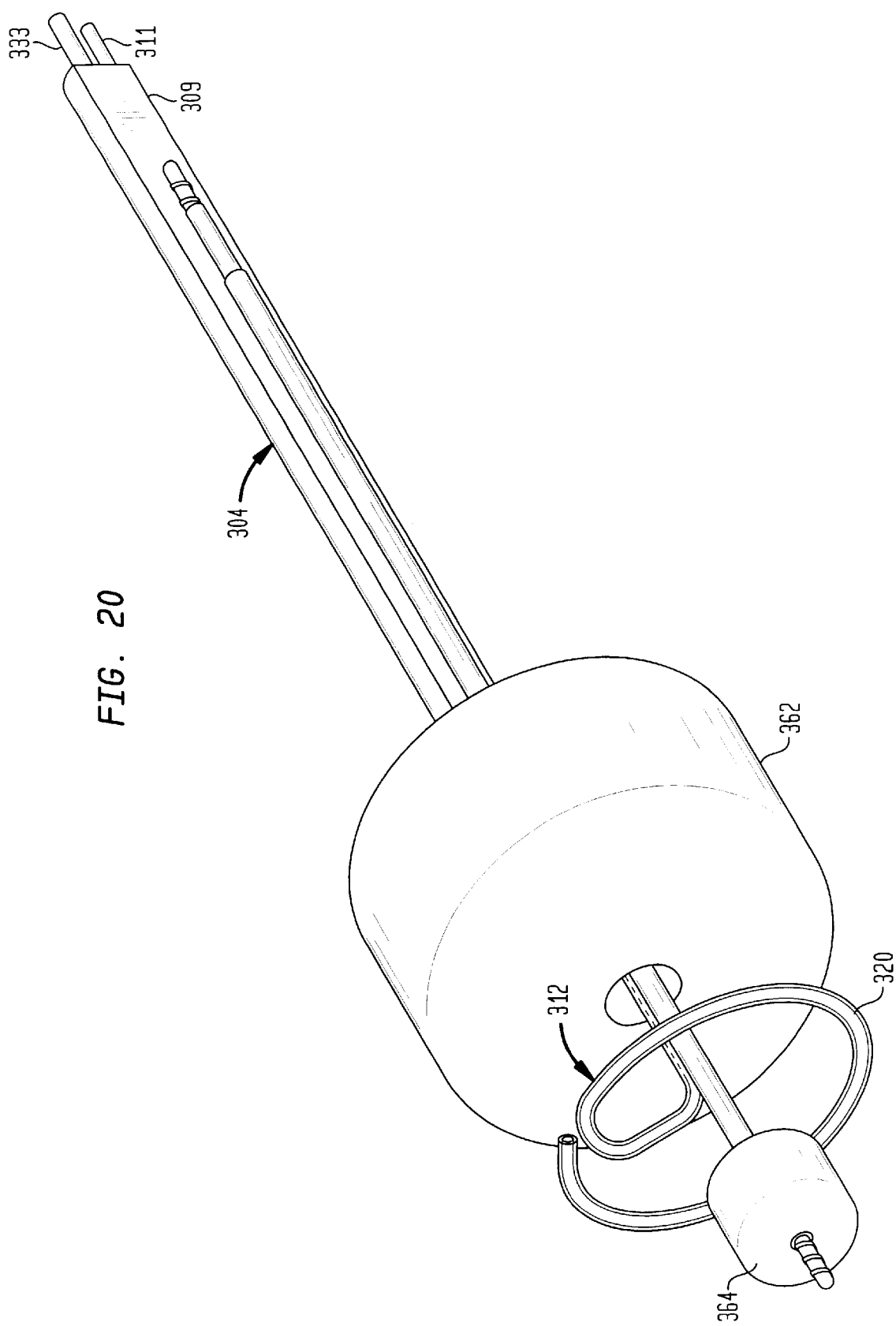
FIG. 20 is a diagrammatic perspective view of the apparatus of FIGS. 14–19 in an assembled condition during one phase of operation.

The expansible positioning element 362 of the pusher catheter is then expanded by inflating it to the condition illustrated in FIG. 20. In this condition, the pusher catheter 331, stabilizer catheter 360 and delivery system catheter 304 form a composite holding structure, with positioning element 362 is movable relative to the anchor 364. The positioning element 362 is thus movable relative to the distal region 312 of the treatment catheter. The distal region, and the elongated transducer array 320 carried thereon, can be biased against the interior of the heart chamber by urging the proximal end 333 of the pusher catheter in the distal direction, thereby engaging positioning element or balloon 362 with the distal region 312 of the treatment catheter. Balloon 362 will bear against all portions of the treatment catheter distal region with substantially uniform pressure, and assure good engagement of the treatment catheter with the chamber wall.

After treatment has been applied with a treatment catheter in one configuration, the expansible positioning structure can be partially or fully collapsed, while leaving the delivery system catheter in place. The distal region of the treatment catheter, and hence the transducer array can be brought to a different configuration and the positioning structure can be expanded again, so that the treatment may be repeated along a different path on the interior surface of the organ. Alternatively, the treatment catheter can be withdrawn and replaced by a different treatment catheter to provide a different configuration of the transducer array while the positioning structure is collapsed, and the treatment can be repeated using the new treatment catheter.

In a variant of this structure, the expansible positioning structure or balloon 362 is carried on the delivery system catheter 302, at head 303, and inflated using a lumen within the delivery system catheter itself. With this alternative structure, the positioning element can be moved relative to the distal region of the treatment catheter by sliding the delivery system catheter along the stabilizer catheter. Thus, the delivery system catheter acts as a pusher catheter. In a further alternative, the catheter carrying the positioning structure can remain fixed relative to the treatment catheter, and the degree of engagement between the positioning structure and the treatment catheter can be controlled by controlling the degree of expansion of the positioning structure, such as the degree of inflation of a balloon constituting the positioning structure.

The procedures and apparatus set forth above can be used to treat linear paths along the wall of a bodily organ instead of, or in addition to, looplike paths. For example, if the distal region of the treatment catheter bearing the transducer array is brought to a straight shape lying along the wall of the heart before the treatment catheter and array are biased into engagement with the wall of the heart, tissue along a linear path can be ablated or otherwise treated. Such a procedure can be used to form a maze of ablated tissue surrounding a region of the cardiac wall, and can also be used in conjunction with ablation of looplike regions to form a composite maze. For example, individual ablated loops each encircling home the ostium of one or more pulmonary veins can be joined by linear ablated paths.

In further variants, the ultrasonic array and treatment catheter can be brought to a looplike shape which encircles the ostia of plural pulmonary veins, and the transducer array can be actuated to ablate tissue in the heart wall along a path surrounding all of these ostia. Such a structure may include a larger positioning balloon or other positioning element. Plural anchors arranged for engagement with plural pulmonary veins can be used with one positioning element. Conversely, the anchor can be omitted.

The elongated ultrasonic transducer and the structures and methods discussed above can be used to treat tissue surrounding other cavernous or tubular internal organs such tissue in the wall or adjacent structures of a blood vessel, a part of the respiratory tract, a part of the digestive tract or a part of the urinary tract as, for example, to ablate a portion of the prostate gland surrounding the urethra or to ablate a sphincter surrounding the urethra or rectum.

A flexible, elongated ultrasonic transducer according to a further embodiment of the invention (FIG. 21) includes an elongated flexible tape 421 wound in a helix around the exterior of a region of a catheter body 420. The tape desirably is a laminate including a relatively high-modulus backing layer such as a metallic layer, one or more layers of a polymeric electromechanical transduction material such as a piezoelectric material, together with two or more metallic electrode layers. The backing layer may serve as one of the electrode layers. The electrode layers, including the backing layer, may be continuous, so that the entire array includes only one continuous transducer element. Alternatively, one or more of the layers may be interrupted so as to provide a plurality of individual transducer elements. Where the layers are continuous, the transducer array will emit uniformly in all radial directions. Individual transducer elements can be positioned on the tape so that they form a strip of transducer elements along one side of the catheter when the tape is wound into the helix. The catheter, with the helical tape, can be flexed in all directions transverse to the direction of elongation of the catheter.

Figure 21:
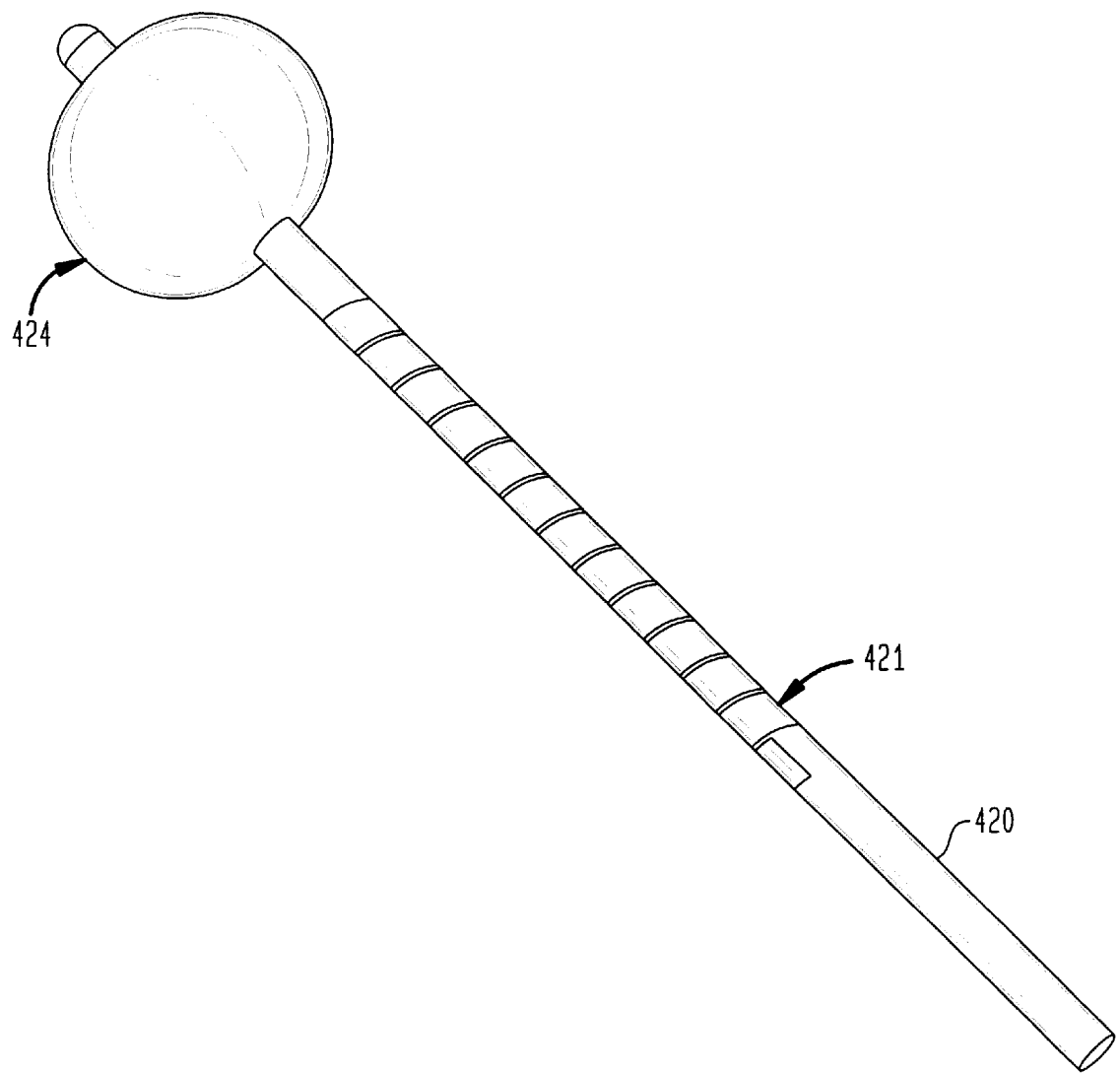
FIG. 21 is a diagrammatic perspective view of a treatment catheter in accordance with a further embodiment of the invention.

An elongated, flexible ultrasonic transducer array as shown in FIG. 21 can be used as part of the apparatus discussed above with respect to FIGS. 1–20. Alternatively, the catheter bearing the transducer element can be provided with a balloon 424 or other suitable anchoring device for use, for example, within the urinary bladder. Such a catheter can be threaded into the urethra and anchored therein by the balloon, and can be used to ablate prostate tissue. Also, the transducer elements discussed above with reference to FIGS. 1–13 can be provided along the length of a catheter as shown in FIG. 21.

The term "catheter" as used herein should be understood in the broad sense as encompassing devices suitable for introduction into the body of a living subject, and hence as including other elongated probes which can be introduced into the body, as, for example, the devices commonly referred to as endoscopes, nasogastric tubes, endotracheal tubes, and the like.

Numerous variations of the features discussed above can be employed. For example, the transducer arrays discussed above can incorporate ceramic piezoelectric materials rather than polymeric materials. For example, ceramic piezoelectric elements can be mounted on a flexible printed circuit similar to those discussed above. Although those regions occupied by the ceramic elements will be substantially rigid, the remainder of the printed circuit can remain flexible. Thus, flexible regions can be provided between adjacent ceramic elements. In the embodiments discussed above with reference to FIGS. 5–9 and with reference to FIG. 10, the ceramic elements can be disposed in the panes, leaving the hinge regions between panes flexible. For example, the treatment catheter need not be separate from the stabilizer catheter. For example, the energy emitter can be disposed on a region of a catheter distal to a positioning balloon. After the distal region carrying the emitter is brought to the desired shape, the balloon is inflated. Inflation of the balloon moves a wall of the balloon distally relative to the catheter, so that this wall engages the shaped distal region of the catheter and forces it into engagement with the wall of the heart. Also, expansible positioning elements other than balloons can be employed as, for example, mechanically expansible structures can be used. The anchor element need not be a balloon; a mechanically expansible element similar to a vascular stent can be employed instead. Such an element provides a benefit in that it does not block blood flow through the blood vessel. The entire transducer array need not be activated simultaneously; where the transducer array includes separate signal inputs for various groups of elements, the groups can be actuated separately. The flexible ultrasonic transducers and treatment catheters can be applied in other techniques. Conversely, the technique of shaping and positioning a treatment catheter before engaging the positioning element can be applied to treatment catheters having operative elements other than ultrasonic transducers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A medical device comprising an elongated catheter body with proximal and distal directions in its direction of elongation and an elongated ultrasonic transducer array extending in said proximal and distal directions, said catheter body and said transducer array being flexible in all directions transverse to said proximal and distal directions.

2. A medical device as claimed in claim 1 wherein said transducer array is substantially in the form of a helix surrounding a region of said catheter body.

3. An elongated ultrasonic transducer array having lengthwise directions, said array including:
   (a) a sheetlike element having a first fold extending in said lengthwise directions and defining a first pair of adjacent regions on opposite sides of the fold, said regions being non-parallel with one another, at least one of said regions being an active region;
   (b) a plurality of ultrasonic transducer elements disposed on or formed integrally with said sheetlike element, said sheetlike element having notches in each of said regions extending along axes transverse to said first fold at locations spaced apart from one another in said lengthwise direction and subdividing each of said regions into panes, the notches in each region of said first pair being offset in said lengthwise direction from the notches in the other region of said first pair, said panes of each region of said first pair having hinge zones aligned with the axes of notches in the other region of said first pair, said sheetlike element being flexible at least in said hinge zones, whereby the array is free to bend in directions transverse to said lengthwise directions.

4. An array as claimed in claim 3 wherein each region of said first pair has a outlying boundary remote from said first fold and the notches in each said region extend from the outlying boundary of that region, to and across said first fold and into the other region of said first pair, but do not extend to the outlying boundary of the other region of said first pair.

5. An array as claimed in claim 3 wherein said sheetlike element has one or more electrical conductors thereon, said conductors extending lengthwise along said sheetlike element in a zigzag pattern so that said conductors pass through the hinge regions of said panes and around said notches.

6. An array as claimed in claim 3 wherein each region of said first pair has a outlying boundary remote from said first fold and the notches in each region extend from the outlying boundary of that region, to and across said first fold and into the other region of said first pair, but do not extend to the outlying boundary of the other region of said first pair.

7. A method of applying energy within the body of a living subject comprising the steps of:
   (a) placing a device including hollow enclosure within the body of the subject;
   (b) providing at least one fluid medium within the hollow enclosure;
   (c) directing energy onto an internal structure of the body through the fluid in said hollow enclosure so that said energy is refracted by one said fluid medium in the enclosure; and
   (d) imaging the body of the subject while said enclosure is disposed in the body of the subject and while the hollow enclosure is filled with one said fluid medium, the fluid disposed in said enclosure having response to said imaging step different from the response of bodily tissue to said imaging step, whereby the fluid-filled enclosure will be seen in contrast in an image resulting from said imaging step.

8. A method as claimed in claim 7 wherein said step of providing at least one fluid medium is performed so that the same fluid medium is disposed in said enclosure during said step of directing energy and during said imaging step.

9. A method as claimed in claim 7 wherein the fluid disposed in said enclosure during said imaging step includes one or more paramagnetic transition metal ions and said imaging step includes magnetic resonance imaging.

10. A method as claimed in claim 7 wherein said step of directing energy includes directing ultrasonic waves through said enclosure so that said ultrasonic waves are refracted by the fluid in said enclosure.

11. Apparatus for applying thermal treatment to tissue of an internal organ of a living subject comprising:
   (a) one or more catheters;
   (b) an elongated energy emitter carried on one of said one or more catheters, said elongated energy emitter being adapted to assume a desired shape when disposed within said organ;
   (c) an expansible positioning structure carried on one of said one or more catheters, said energy emitter in said desired shape extending over said expansible positioning structure so that said expansible positioning structure can bias said elongated energy emitter against a wall of the organ, whereby when said positioning element and said energy emitter are in an operative condition, said energy emitter in said desired shape extends along an elongated path having a shape corresponding to said desired shape on such interior wall, said energy emitter being operative to emit energy at a plurality of locations along its length so as to heat tissue surrounding said organ at a plurality of locations along said path.

12. Apparatus as claimed in claim 11 wherein said energy emitter is adapted to emit energy substantially simultaneously at said plurality of locations along its length to thereby heat tissue at a plurality of locations along said path substantially simultaneously.

13. Apparatus as claimed in claim 11 wherein said expansible positioning element and said energy emitter are adapted for operation within a heart chamber of a mammalian subject, said expansible positioning element biasing said energy emitting element against the interior wall of such heart chamber in said operative condition.

14. Apparatus as claimed in claim 11 wherein said expansible positioning structure includes a balloon.

15. Apparatus as claimed in claim 11 wherein said elongated energy emitter includes one or more ultrasonic transducer elements.

16. Apparatus as claimed in claim 15 wherein said ultrasonic transducer elements include a polymeric electromechanical transduction film.

17. Apparatus as claimed in claim 16 wherein said electromechanical transduction film is a polymeric piezoelectric film.

18. Apparatus as claimed in claim 15 wherein said one or more ultrasonic transducer elements includes an elongated ultrasonic transducer array having a lengthwise axis, said array being flexible in directions transverse to its lengthwise axis and extending in said desired curved shape in said operative condition.

19. Apparatus as claimed in claim 18 wherein said ultrasonic transducer array includes active emitting regions facing generally in a radially-outward direction transverse to the lengthwise axis of the array.

20. Apparatus as claimed in claim 11 wherein said energy emitter is formed separately from said expansible positioning structure, so that said energy emitter can assume said desired shape before it is biased against the wall of the organ.

21. Apparatus as claimed in claim 20 wherein said energy emitter is adapted to assume a curved shape.

22. Apparatus as claimed in claim 21 wherein said energy emitted is adapted to form a loop, whereby said path will be generally in the form of a loop.

23. Apparatus as claimed in claim 11 wherein said one or more catheters includes a treatment catheter carrying said emitting device, said emitting device extending lengthwise along said treatment catheter adjacent the distal end thereof.

24. Apparatus as claimed in claim 23 wherein said anchor includes an expandable anchor element movable between a collapsed condition and an expanded condition.

25. Apparatus as claimed in claim 23 wherein said expansible positioning structure is movable relative to said treatment catheter while said treatment catheter is in said operative condition.

26. Apparatus as claimed in claim 23 wherein said one or more catheters include a holding structure separate from said treatment catheter, said holding structure carrying said expansible positioning element.

27. Apparatus as claimed in claim 26 wherein said holding structure includes a stabilizer catheter and an anchor linked to said stabilizer catheter, said anchor being adapted to engage an anatomical structure in or adjacent said organ.

28. Apparatus as claimed in claim 27 wherein said expansible positioning element is mounted on said stabilizer catheter.

29. Apparatus as claimed in claim 27 wherein said expansible positioning element is movable relative to said anchor while said anchor is engaged with said anatomical structure.

30. A method of applying thermal treatment to tissue of an internal organ comprising:
(a) inserting an elongated energy emitter into the interior of the internal organ and bringing the energy emitter to a desired shape in a desired position relative to the organ;
(b) inserting an expansible positioning element into the interior of the organ; and
(c) expanding said positioning structure so that the energy emitter is disposed between the positioning structure and the wall of the organ and said positioning structure biases said energy emitter against the interior wall of the organ, whereby said energy emitter in said desired shape extends along an elongated path having a shape corresponding to said desired curved shape on such interior wall; and
(d) while said energy emitter is extending along said path, actuating said energy emitter to emit energy at a plurality of locations along its length so as to heat tissue at a plurality of locations along such path.

31. A method as claimed in claim 30 wherein said energy emitter is brought at least approximately to said desired shape and at least approximately to said desired position before said positioning structure is fully expanded.

32. A method as claimed in claim 31 wherein said desired shape is a curved shape.

33. A method as claimed in claim 32 wherein said desired shape a closed or nearly closed loop.

34. A method as claimed in claim 30 wherein said energy emitter emits energy substantially simultaneously at said plurality of locations along its length to thereby heat tissue at a plurality of locations along said path substantially simultaneously.

35. A method as claimed in claim 34 wherein said energy emitter includes an array of one or more ultrasonic transducer elements, said array extending lengthwise along the device, said transducer elements emitting ultrasonic energy at said plurality of locations.

36. A method as claimed in claim 35 wherein said step of inserting said energy emitter includes the step of advancing the array lengthwise through a tubular anatomical structure and then deforming the array in directions transverse to its lengthwise direction to said desired shape.

37. A method as claimed in claim 35 further comprising focusing ultrasonic energy emitted by said transducer elements onto a elongated focal region extending generally parallel to said path.

38. A method as claimed in claim 37 wherein said focal region is disposed on or in the wall of said organ.

39. A method as claimed in claim 38 further comprising varying the focus of said ultrasonic energy so as to move said focal region towards or away from said array and thereby position said focal region deeper or shallower within the wall of said organ while said array remains substantially in position along said path.

40. A method as claimed in any one of claim 30 or claim 32 or claim 36 wherein said internal organ is the heart, and wherein said heating is effective to kill tissue within the wall of a chamber of the heart.

41. A method as claimed in claim 40 wherein said heating is effective to kill tissue substantially through the wall of the heart.

42. A method as claimed in claim 40 further comprising the step of moving said expansible positioning element toward said emitter so as to bring the positioning element into engagement with the emitter after said emitter is at least approximately in said desired shape and desired position.

43. A method as claimed in claim 40 wherein said path at least partially encircles the ostium of at least one blood vessel opening to such chamber of the heart.

44. A method as claimed in claim 43 wherein said path substantially completely encircles said at least one ostium.

45. A method as claimed in claim 40 further comprising the step of placing at least one anchoring element within at least one said blood vessel, said at least one anchoring element being connected to said positioning structure at least while the positioning structure is biasing the energy-emitter against the wall of the heart so that said anchoring element tends to retain the positioning structure and the emitter in position.

46. A method as claimed in claim 45 wherein said anchoring element and said positioning structure are both attached to a stabilizer catheter, the method further comprising the step of placing said stabilizer catheter so that the anchoring element is disposed within said blood vessel and the positioning structure is disposed within the chamber, and then engaging the anchoring element with the wall of the blood vessel and expanding the positioning structure.

47. An array as claimed in claim 46 wherein said ultrasonic transducer elements include polymeric piezoelectric film overlying or formed integrally with said sheetlike element.

48. A medical device comprising an elongated catheter body with proximal and distal directions in its direction of elongation, and an array as claimed in claim 39, the lengthwise directions of said array and said fold extending in the proximal and distal directions of said body, said active region being disposed on or constituting an outwardly-facing surface of said body and extending in lateral directions transverse to said lengthwise directions.

49. A device as claimed in claim 48 wherein said regions of said sheetlike element including at least one additional region extending from said first fold into the interior of said body in a direction transverse to said lateral and lengthwise directions.

50. A device as claimed in claim 48 wherein said sheetlike element includes first and second active regions disposed on opposite sides of said first fold, said transducer elements being disposed in both of said active regions.

51. A device as claimed in claim 50 wherein said active regions slope radially outwardly in opposite lateral directions away from said first fold whereby said transducer elements on said first and second regions face toward a common elongated focal region outside of said body but generally parallel thereto.

52. A device as claimed in claim 50 wherein said first and second active regions join one another at said first fold.

53. A device as claimed in claim 50 wherein said sheetlike element includes second and third folds extending generally parallel to said first fold, a first additional region joining said first active region at said first fold and a second additional region joining said first additional region at said second fold, said second active region joining said second additional region at said third fold, whereby said second active region and said second additional region constitute a second pair of mutually adjacent regions, said additional regions extending into the interior of said body.

54. A device as claimed in claim 53 wherein said sheetlike element has notches in each of said regions extending transverse to said folds and transverse to said lengthwise direction, the notches in said additional regions being aligned with one another in said lengthwise direction, the notches in said second active region being offset in said lengthwise direction from the notches in said second additional region.

55. A medical device comprising:
  (a) a first elongated catheter body having an exterior surface and having proximal and distal directions;
  (b) a distributed array of one or more ultrasonic transducer elements disposed on or constituting a portion of said exterior surface of said first body and extending in said proximal and distal directions; and
  (c) an elongated lens overlying said array of transducer elements and extending in said proximal and distal directions, said lens being adapted to focus ultrasonic emissions from said transducer elements into a elongated focal region outside of said body but generally parallel thereto, said body, lens and array being flexible in directions transverse to said proximal and distal directions.

56. A medical device as claimed in claim 55 wherein said lens includes a hollow enclosure extending in said proximal and distal directions, said enclosure being filled with a lens fluid when the device is in an operative condition.

57. A medical device as claimed in claim 56 wherein said hollow enclosure is deformable, whereby the shape of said lens can be varied by varying the pressure of said lens fluid.

58. A medical device as claimed in claim 56 wherein said lens fluid includes an X-ray or magnetic-resonance contrast medium.

59. A medical device as claimed in claim 56 further comprising ports communicating with said hollow enclosure proximal to and distal to said transducer array so that a fluid can be circulated through said hollow enclosure to control the temperature of said transducer array.

60. A medical device as claimed in claim 48 or claim 55 wherein said catheter body is hollow and defines a catheter bore, said catheter bore being filled with a catheter bore fluid when said device is in an operative condition, at least said portion of said catheter body being deformable so as to vary the configuration of said array by varying the pressure of said catheter bore fluid.

* * * * *

UNITED STATES PATENT AND TRADEMARK OFFICE
CERTIFICATE OF CORRECTION

PATENT NO. : 6,605,084 B2
DATED : August 12, 2003
INVENTOR(S) : David E. Acker et al.

It is certified that error appears in the above-identified patent and that said Letters Patent is hereby corrected as shown below:

Column 23,
Line 21, "claim 39" should read -- claim 3 --.

Signed and Sealed this

Sixteenth Day of December, 2003

JAMES E. ROGAN
*Director of the United States Patent and Trademark Office*